US011519849B2

(12) United States Patent
Langland et al.

(10) Patent No.: US 11,519,849 B2
(45) Date of Patent: Dec. 6, 2022

(54) METHANE PEAK DETECTION

(71) Applicant: Aclima Inc., San Francisco, CA (US)

(72) Inventors: Todd Langland, Mill Valley, CA (US); Meghan Elizabeth Thurlow, San Francisco, CA (US); Davida Herzl, San Francisco, CA (US); Brian LaFranchi, Berkeley, CA (US); Robert Murphy, Alameda, CA (US)

(73) Assignee: Aclima Inc., San Francisco, CA (US)

( * ) Notice: Subject to any disclaimer, the term of this patent is extended or adjusted under 35 U.S.C. 154(b) by 50 days.

(21) Appl. No.: 16/922,929

(22) Filed: Jul. 7, 2020

(65) Prior Publication Data

US 2021/0010929 A1    Jan. 14, 2021

Related U.S. Application Data

(60) Provisional application No. 62/871,473, filed on Jul. 8, 2019.

(51) Int. Cl.
*G01N 21/31*    (2006.01)
*G01N 33/00*    (2006.01)
*G01D 21/02*    (2006.01)

(52) U.S. Cl.
CPC ............. *G01N 21/31* (2013.01); *G01D 21/02* (2013.01); *G01N 33/004* (2013.01); *G01N 2021/3196* (2013.01)

(58) Field of Classification Search
CPC .............. G01N 21/31; G01N 33/004; G01N 2021/3196; G01N 33/0047; G01N 33/225; G01N 33/0004; G01D 21/02

USPC ......................................................... 340/632
See application file for complete search history.

(56) References Cited

U.S. PATENT DOCUMENTS

| 4,507,558 | A | | 3/1985 | Bonne | |
|---|---|---|---|---|---|
| 5,783,741 | A | * | 7/1998 | Ellis | G01N 30/84 422/89 |
| 5,946,095 | A | | 8/1999 | Henningsen | |
| 2019/0212314 | A1 | * | 7/2019 | Lu | G01N 33/225 |
| 2021/0255153 | A1 | * | 8/2021 | Leigh | G01N 30/88 |

OTHER PUBLICATIONS

By "Exploratory study of atmospheric methane enhancements derived from natural gas use in the Houston urban area" by Sanchez et al. (Year: 2018).*
"A Mobile Sensing Approach for Regional Surveillance of Fugitive Methane Emissions in Oil and Gas Production" by Albertson, et al. (Year: 2016).*
"Mobile Laboratory Observations of Methane Emissions in the Barnett Shale Region" by Yacovitch, et al. (Year: 2015).*
(Continued)

*Primary Examiner* — Omar Casillashernandez
(74) *Attorney, Agent, or Firm* — Van Pelt, Yi & James LLP

(57) ABSTRACT

A method for monitoring air quality is described. The method includes measuring ethane and methane using a mobile sensor platform to provide sensor data. The sensor data includes methane data and ethane data captured at a nonzero mobile sensor platform speed. Methane and ethane peak(s) are identified in the sensor data. Correlation(s) between the methane and ethane peak(s) and/or between the methane peak(s) and at least one amount of $^{13}C$ are determined. A source for the methane is determined based on the correlation.

20 Claims, 11 Drawing Sheets

(56) References Cited

OTHER PUBLICATIONS

"Dual-Gas Sensor of CH4/C2H6 Based on Wavelength Modulation Spectroscopy Coupled to a Home-Made Compact Dense-Pattern Multipass Cell" by Tian et al. (Year: 2019).*
Albertson et al., A Mobile Sensing Approach for Regional Surveillance of Fugitive Methane Emissions in Oil and Gas Production, Environmental Science & Technology, 2016 American Chemical Society, pp. 2487-2497.
Lopez et al., Isotopic Signatures of Anthropogenic Ch4 Sources in Alberta Canada, Atmospheric Environment, vol. 164, 2017, pp. 280-288.
Peischl et al., Quantifying Methane and Ethane Emissions to the Atmosphere from Central and Western U.S. Oil and Natural Gas Production Regions, Journal of Geophysical Research: Atmospheres, AGU 100 Advancing Earth and Space Science, Jul. 20, 2018, pp. 7725-7740.
Sanchez et al., Exploratory Study of Atmospheric Methane Enhancements Derived from Natural Gas Use in the Houston Area, Mar. 2018, pp. 1-32.
Subramanian et al., Methane Emissions from Natural Gas Compressor Stations in the Transmission and Storage Sector: Measurements and Comparisons with the EPA Greenhouse Gas Reporting Program Protocol, Feb. 10, 2015, pp. 3252-3261.
Tian et al., Dual-Gas Sensor of CH4/C2H6 Based on Wavelength Modulation Spectroscopy Coupled to a Home-Made Compact Dense-Pattern Multipass Cell, Sensor, MDPI, Feb. 17, 2019.
Yacovitch et al., Demonstration of an Ethane Spectrometer for Methane Source Identification, Environmental Science & Technology, Jun. 19, 2014, vol. 48, pp. 8028-8034.
Yacovitch et al., Mobile Laboratory Observations of Methane Emissions in the Barnett Shale Region, Environmental Science and Technology, 2015 American Chemical Society, pp. 7889-7895.
Weller et al., An Open Source Algorithm to Detect Natural Gas Leaks from Mobile Methane Survey Data, PLOS One, Research Article, Published Feb. 13, 2019, pp. 1-18.

* cited by examiner

METHANE PEAK DETECTION

CROSS REFERENCE TO OTHER APPLICATIONS

This application claims priority to U.S. Provisional Patent Application No. 62/871,473 entitled METHANE PEAK DETECTION filed Jul. 8, 2019 which is incorporated herein by reference for all purposes.

BACKGROUND OF THE INVENTION

Environmental monitoring measures the levels of pollutants in the surroundings (e.g. the air) and detects potentially harmful pollution. One such pollutant is methane ($CH_4$). Methane not only adversely affects air quality for nearby humans, but is also a greenhouse gas. Methane is emitted from a variety of natural and anthropogenic sources and is a significant component of natural gas. It is desirable, therefore, to detect sources of methane, such as natural gas leaks. Natural gas leaks may occur at various stages of production and delivery, from extraction of natural gas at a wellhead to delivery systems that transport processed natural gas to end users. In order to detect natural gas leaks, various technologies may be used. At the wellhead, stationary methane ($CH_4$) sensors or infrared imaging systems are used to detect large leaks. For leaks in delivery systems (i.e. pipelines), existing vehicle-mounted systems may search for methane ($CH_4$) leaks while a vehicle is in motion. Upon detecting a threshold amount of methane, the vehicle is stopped and a search is done for ethane ($C_2H_6$). If ethane and methane are detected in the appropriate fractions while the detector is stationary, then natural gas is considered to be detected.

Although such conventional systems are capable of locating some natural gas leaks, they are susceptible to various drawbacks. Consequently, an improved mechanism for detecting sources of methane, such as natural gas leaks, is desired.

BRIEF DESCRIPTION OF THE DRAWINGS

Various embodiments of the invention are disclosed in the following detailed description and the accompanying drawings.

DETAILED DESCRIPTION

Figure 1:
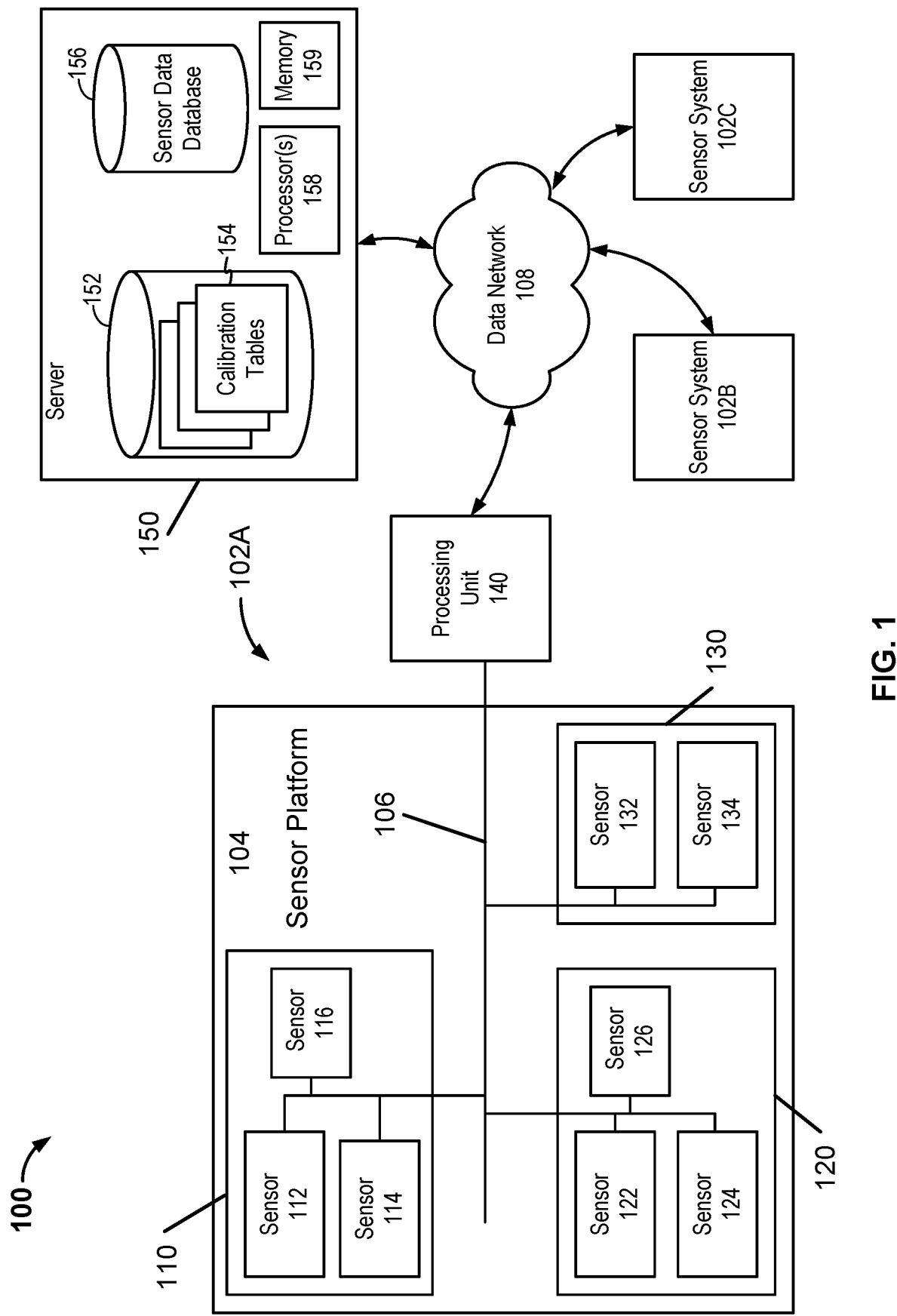
FIG. 1 depicts an embodiment of a system for collecting and processing environmental data.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Environmental data includes measurements of pollutants, contaminants and/or other components of the environment. Environmental quality can be assessed based on this environmental data and is a measure of the suitability of the surroundings for humans and/or other lifeforms. An important aspect of environmental quality is air quality. Environmental data thus includes but is not limited to measurements related to air quality (e.g. the presence or absence of various pollutants in the air) as well as other features of the surroundings. For example, one such pollutant that relates to air quality and climate change is methane ($CH_4$). Because methane is present in natural gas, natural gas leaks are one source of methane pollutants. Natural gas leaks may occur at wellheads where natural gas is extracted, in upstream delivery systems that transport natural gas from the wellhead to processing systems, at processing systems that refine natural gas, and in delivery systems that provide natural gas (i.e. refined, processed natural gas) to end users. As such, it is desirable to detect and characterize natural gas leaks.

Various technologies are used to detect natural gas leaks. At the wellhead, leaks are often large and, therefore, both costly and a significant source of $CH_4$. Stationary $CH_4$ sensors or infrared imaging systems are used to search for large leaks at the wellhead. Stationary $CH_4$ sensors can detect large quantities of natural gas escaping. Infrared imaging systems may be used to attempt to optically localize the source of a leak at the wellhead. If the imaging system or the stationary methane sensor indicates that $CH_4$ is detected, a leak is considered to be discovered. For leaks in delivery systems (i.e. pipelines), existing vehicle-mounted systems may search for $CH_4$ leaks while a vehicle is in motion. Upon detecting a threshold amount of $CH_4$, the vehicle is stopped and a search is done for ethane ($C_2H_6$). If ethane and methane are detected in the appropriate fractions while the detector is stationary, then natural gas is considered to be detected.

Although such conventional systems are capable of locating some natural gas leaks, they can only be deployed infrequently due to cost and complexity. Further, such techniques may be subject to errors, may miss leaks that are smaller in size, may be unable to detect leaks in pipelines or other delivery systems, may miss leaks that extend over larger areas, are time consuming and are susceptible to other issues. Consequently, an improved mechanism for detecting natural gas leaks is desired.

A technique for monitoring environmental quality is described. The technique may be considered a mechanism for monitoring $CH_4$ and, therefore, the effect of $CH_4$ on air quality. The technique includes measuring ethane ($C_2H_6$) and methane using a mobile sensor platform to provide sensor data. The sensor data includes methane data and ethane data captured at a nonzero mobile sensor platform speed. In some embodiments, the ethane and the methane data include data captured at a mobile sensor platform speed of at least five miles per hour. In some embodiments, the speed is at least ten miles per hour. In some embodiments, the speed does not exceed thirty four miles per hour. For example, in some embodiments, the speed is at least three meters per second and not more than fifteen meters per second (6 mph-34 mph). In some embodiments, the methane and ethane data consists of data captured at nonzero mobile sensor platform speeds. The methane and ethane data may also consist of data that is captured passively, without user intervention in the data capture process.

Methane and ethane peak(s) are identified in the sensor data. Correlation(s) between the methane and ethane peak(s) and/or between at least one amount of $^{13}C$ and the at least one methane peak are determined. A source for the methane is determined based on the correlation. The correlation includes at least one of a correlation in peak shape, peaks being temporally co-located, peaks being geographically co-located, and peaks having the appropriate ratio for a particular type of methane source. In some embodiments, the mobile sensor platform speed is accounted for, e.g. in identifying the methane and ethane peaks and/or determining the correlation between the method and ethane peaks. In order to determine the correlation between the methane and ethane, a ratio range of ethane to methane to methane may be calculated. In such embodiments, identifying the source further includes identifying the source based on the ratio range. For example, a natural gas source may be determined to exist if the ratio range is at least one percent and not more than six percent. A thermogenic source, such as a wellhead of natural gas, may be determined to exist if the ratio range is greater than six percent. A non-natural gas source, such as a landfill or other biogenic source, may be determined to exist if the ratio range is less than one percent. In some embodiments, other and/or additional sources may be identified based on the ratio range. In some embodiments, it is also determined whether a coincident CO peak is lacking for the methane and ethane peak(s). In such embodiments, the source is identified as a natural gas source only if the coincident CO peak is also lacking. In some embodiments, a coincident CO peak is considered indicative of the methane being due to vehicle (e.g. automobile) emissions.

The sensor data may also be further analyzed. For example, the source location may be determined based on the source identified, the corresponding methane peak(s), the corresponding ethane peak(s), a wind speed and a wind direction. Clustering may be performed for the methane peak(s), the ethane peak(s) and/or the sources.

In addition, a baseline for methane and/or ethane may be determined. Determination of the baseline allows for identification of methane and/or ethane peaks. In some embodiments, a rolling baseline is determined based on the median of ethane and methane measured for a particular amount of time (i.e. a baseline time period), such as twenty seconds through one minute (e.g. thirty seconds). In some embodiments, the size of the baseline time period and thus the area corresponding to the baseline may be modified. For example, the baseline time period over which methane and/or ethane data is captured and used to determine a baseline may be modified to account for elevated readings in a particular region. In such an embodiment, a region corresponding to elevated methane and elevated ethane is identified. Such a region has an area corresponding to the square of a quantity. The quantity is the mobile sensor platform speed multiplied by the baseline time period (e.g. thirty seconds). The methane and ethane baselines for the region are recalculated using a new, larger time period (e.g. greater than one minute and not more than four minutes). The methane baseline is a median of methane data for the region collected using the larger time. The ethane baseline is the median of ethane data for the region collected using the larger time. Ethane and methane thresholds are set based on the ethane and methane baselines. The ethane and methane thresholds are greater or equal to the baselines. In some embodiments, the value of the ethane and methane thresholds may be used to tune the sensitivity of detection. Lower ethane and methane thresholds allow for increased sensitivity of peak detection. Thus, a methane peak may be identified as sensor data including multiple methane readings in the region greater than the methane threshold. Similarly, an ethane peak may be identified as sensor data including multiple ethane readings in the region greater than the ethane threshold. The methane peak has a location based on a methane weighted average of the multiple methane readings. Similarly, the ethane has a location based on an ethane weighted average of the multiple ethane measurements. In some embodiments, the methane and/or ethane peak has a location selected to be the maximum concentration of the peak.

In some embodiments, a system including a processor and a memory coupled to the processor and configured to provide the processor with instructions. In such embodiments, the processor is configured to receive sensor data captured using a mobile sensor platform. The sensor data includes methane data and ethane data captured at a nonzero mobile sensor platform speed. The processor is configured to identify methane and ethane peak(s) and determine correlation(s) between the methane and ethane peak(s). The processor is further configured to identify a source for the methane based on the correlation. The correlation includes at least one of a correlation in peak shape, peaks being temporally co-located, peaks being geographically co-located, and peaks having the appropriate ratio for a particular type of methane source. In order to determine the correlation between the methane and ethane, a ratio range of ethane to methane may be calculated. In such embodiments, the processor is further configured to calculate the ratio ranges and identify the source based on the ratio range. In some embodiments, it is also determined whether a coincident CO peak is lacking for the methane and ethane peak(s). In such embodiments, the source is identified as a natural gas source only if the coincident CO peak is also lacking. The sensor data may also be further analyzed utilizing the processor. For example, the source location may be modeled and clustering may be performed for the methane peak(s), the ethane peak(s) and/or the sources. Thus, methane may be detected, methane peaks identified, and sources of methane determined. Thus, monitoring of the presence of methane and the corresponding air quality may be facilitated.

FIG. 1 depicts an embodiment of a system 100 for collecting and processing environmental data. System 100 includes multiple sensor systems 102A, 102B, 102C (collectively or generically 102) and server 150. Although a single server 150 is shown, multiple servers may be used. Similarly, although three sensor systems 102A, 102B and 102C are shown, another number are typically present. Sensor systems 102A, 102B and 102C communicate with server 150 via a data network 108. The communication may take place wirelessly.

Sensor system 102A, 102B and 102C may be mobile, for example mounted in a vehicle, or stationary. Sensor system 102A includes a sensor platform 104 having a bus 106 and sensor groups 110, 120 and 130. Group 110 includes sensors 112, 114 and 116; group 120 includes sensors 122, 124 and 126; and group 130 includes sensors 132 and 134. Although particular numbers of sensors are shown in each group 110, 120 and 130, another number of sensors might be used. Further, although three groups 110, 120 and 130 of sensors are shown, another number of groups of sensors (fewer or more) may be present on sensor platform 104. Each group 110, 120 and 130 may include sensors that are co-located. Sensors 112, 114 and 116 are co-located. Sensors 122, 124 and 126 are co-located. Sensors 132 and 134 are co-located. Sensors that are co-located sense the same packet of air under substantially the same conditions.

Sensor systems 102B and 102C are analogous to sensor system 102A. In some embodiments, sensor systems 102B and 102C have the same components as sensor system 102A. However, in other embodiments, the components may differ. For example, sensor system 102B may include some or all of the same sensors/sensor groups as sensor system 102A, but may include sensors not on sensor platform 104.

Server 150 includes calibration database 152 having calibration tables 154, sensor data database 156, processor(s) 158 and memory 159. Processor(s) 158 may include multiple cores. Processor(s) 158 may include one or more central processing units (CPUs), one or more graphical processing units (GPUs) and/or one or more other processing units. Memory 159 can include a first primary storage, typically a random access memory (RAM), and a second primary storage area, typically a non-volatile storage such as solid state drive (SSD) or hard disk drive (HDD). Memory 159 stores programming instructions and data for processes operating on processor(s) 158. Primary storage typically includes basic operating instructions, program code, data and objects used by processor(s) 158 to perform their functions. Primary storage devices (e.g., memory 159) may include any suitable computer-readable storage media, described below, depending on whether, for example, data access needs to be bi-directional or uni-directional Sensor data database 156 includes data received from sensor systems 102A, 102B and/or 102C. After capture by sensor system 102A, 102B and/or 102C, data stored in sensor data database 156 may be operated on by various analytics and visualized. Calibration database 152 and calibration tables 154 are used to correct sensor data from sensor systems 102A, 102B and 102C.

One or more of sensor systems 102A, 102B and 102C may be used to detect methane and, in some embodiments, ethane and CO. Stated differently, sensor systems 102A, 120B and 102C may be used to detect natural gas. Data collected by sensor system(s) 102A, 102B and/or 102C may be processed at the sensor system(s) 102A, 102B and/or 102C (e.g. by processing unit 140) and may undergo processing at server 150.

Figure 2A:
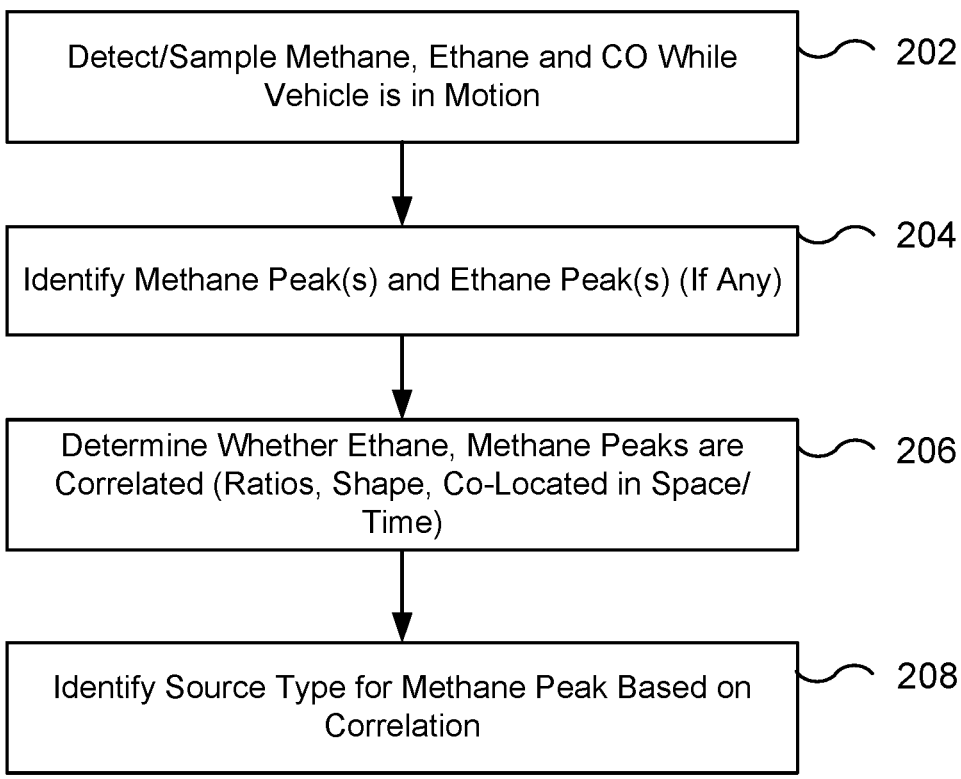
FIGS. 2A-2B are flow charts depicting embodiments of methods for monitoring the effect of methane on environmental quality.
Figure 2B:
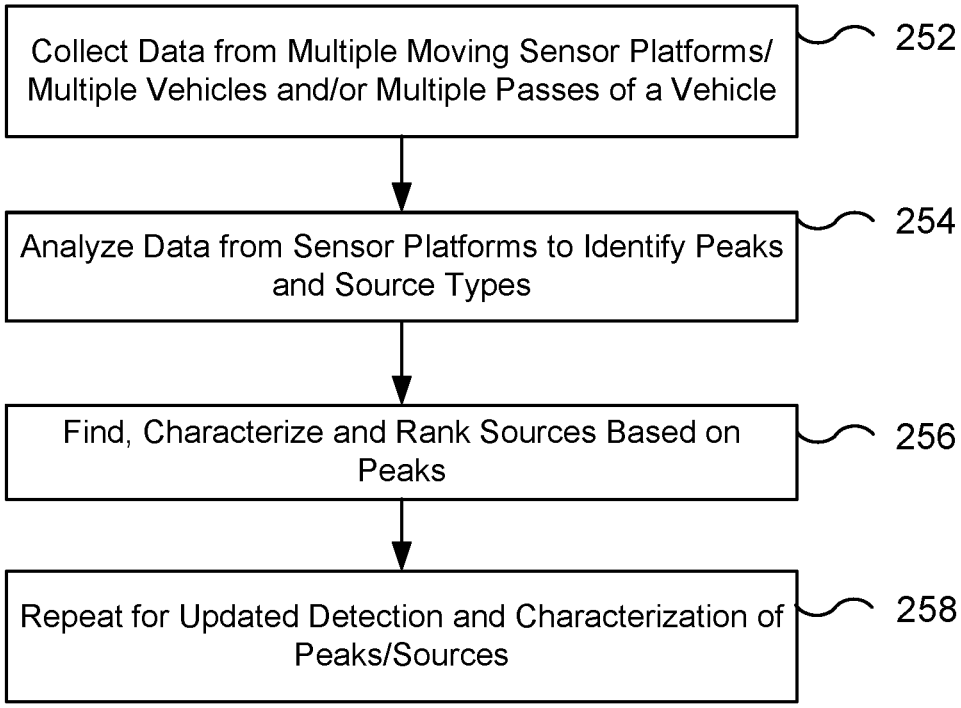

FIGS. 2A-2B are flow charts depicting embodiments of methods 200 and 250, respectively, for monitoring the effect of methane on environmental quality. FIG. 2A depicts an embodiment of method 200 for that may be used by one or multiple mobile sensor platforms. FIG. 2B depicts an embodiment of method 250 that utilizes multiple mobile sensor platforms on multiple vehicles. Referring to FIG. 2A, only some portions of method 200 are described. Moreover, processes in method 200 may include sub-processes and/or may be performed in another order (including in parallel). Method 200 may utilize system 100. A sensor system such as sensor system 102A, 102B, 102C and/or analogous sensor systems placed on a vehicle may be employed for detection. Thus, a mobile platform may be used. Data from individual sensor systems are used (e.g. data from 102A is used to find peaks sensed by sensor system 102A). Further, as described below, method 200 may be carried out on multiple sensor systems, such as sensor systems 102A, 102B and 102C. Thus, data may be obtained by multiple sensor systems carried by multiple vehicles may be analyzed together for detection of methane, ethane, CO, and natural gas. Method 200 may be extended to detection of other substances and determination of leaks/sources of the substances.

Sensor data is accrued while the mobile sensor platform is in motion, at 202. Thus, methane and ethane are sampled. At 202, at least some of the methane and ethane measurements are made while the vehicle is in motion. In some embodiments, CO is also sampled while the vehicle is in motion. Thus, $CH_4$, $C_2H_6$ and CO may be detected by a mobile platform. In some embodiments, data are sampled at a frequency of at least 0.5 Hz and not more than 2 Hz. In some embodiments, data are sampled at 1 Hz. In some embodiments, data for $CH_4$, $C_2H_6$ and/or CO are sampled directly. In some embodiments, data for $CH_4$, $C_2H_6$ and/or CO may be indirectly sampled. In some embodiments, a technique other than ethane concentration (discussed below) may be used to differentiate the sources of methane. For example, carbon isotopes can be used to distinguish methane in natural gas from methane due to other sources such as landfill and vehicle emissions. In such embodiments, the carbon isotopes may be sensed at the same or at different (e.g. lower) frequencies as methane. For example, carbon isotopes may be measured at a frequency of 0.1-0.3 Hz when methane is measured at 1 Hz. In such embodiments, a single isotope measurement may correspond to multiple methane measurements. In some embodiments, multiple isotope sensing subsystems may be used with a single methane sensor. Thus, a sample may be alternately routed to the isotope sensors in order to improve the frequency of isotope detection. In other embodiments, isotope measurements may be made in response to detecting an amount of methane that is greater than some threshold. In some embodiments, additional and/or other substances may also be detected at 202. Further, data is passively sampled at 202. In some embodiments, therefore, the data may simply be collected without user intervention. For example, the driver need not stop the vehicle upon detection of methane to search for ethane. Instead, data is collected as the vehicle travels over a region and/or in motion. Stops by the driver may be made for other reasons (e.g. stop signs, traffic signals, etc.). Thus, the data may be passively captured during routine vehicle operation by individuals, as fleet vehicles or as part of a network of vehicles (e.g. vehicles that are distributed and may be independently as opposed to centrally operated, but which may be in communication with each other or with a central system). In some embodiments, the route taken by the vehicle at 202 is selected based on various criteria. For example, a route may be selected to evenly cover an area or to focus on regions at which methane is more likely to occur. The route may be updated during operation of the vehicle. For example, in response to regions in which the $CH_4$ and/or $C_2H_6$ detected is high, part of the route may be re-traversed. In some embodiments, there may be no route specified for the purposes of data collection. Instead, data is collected as the vehicle travels through the routes selected by the operator. For example, the sensor system may be mounted in a private individual's vehicle and data collected as the private individual travels in the vehicle to carry out their own tasks. In addition to pollutants such as $CH_4$ and/or $C_2H_6$, other data may be collected as part of 202. For example, the time each sample is taken (i.e. a time stamp) and the location of each sample can be measured and recorded. In some embodiments, 202 includes sending the sensor data from the mobile sensor platform to a centralized or other data processing system.

The data are processed at 204, 206 and 208. In some embodiments, 204, 206 and 208 are performed asynchronously with 202. For example, one or more mobile sensor platforms such as systems 102, may collect and transmit data to a centralized system 10 for processing at 202. After some or all of the data is received at the processing system, 204, 206 and 208 are performed. $CH_4$ and $C_2H_6$ peaks (if any) are identified from the sensor data, at 204. In some embodiments, CO peaks are also identified as part of 204. Identification of peaks includes determining whether the amount of the corresponding pollutant (e.g. $CH_4$ and $C_2H_6$) exceeds a threshold for that pollutant. In some embodiments, the threshold for the pollutant is based on a rolling baseline. The rolling baseline is the median of the measurements of the pollutant for a given time window (e.g. thirty seconds, a minute, two minutes, or four minutes) around the time the sample(s) were captured. In some embodiments, the threshold may be selected to be at least the baseline. Lower thresholds generally have a higher sensitivity to the pollutant being detected and may result in more peaks being identified.

It is also determined whether the $CH_4$ and $C_2H_6$ peaks are correlated, at 206. $CH_4$ and $C_2H_6$ peaks being correlated includes at least one of a correlation in peak shape, peaks being temporally co-located, peaks being geographically co-located, and peaks having the appropriate ratio for a particular type of methane source. For example, $CH_4$ and $C_2H_6$ peaks may correspond to (e.g. be measured at) the same location (i.e. are geographically co-located), may correspond to the same time (i.e. are temporally co-located) and/or have characteristics consistent with being from the same source. Such peaks are considered correlated. In some embodiments, the methane peak is considered to have a location based on a methane weighted average of the multiple methane readings. Similarly, the ethane is considered to have a location based on an ethane weighted average of the multiple ethane measurements. Other locations (e.g. the maximum reading) may be selected as the peak location in some embodiments. The locations of these peaks may be correlated (e.g. considered to be at the same location/be co-located if determined to be within a particular distance, such as less than thirty meters, of each other). In some embodiments, the locations of the peaks may be determined and correlated to within ten meters. In some embodiments, the locations of the peaks may be determined and correlated to within six meters. In some embodiments, $CH_4$ and $C_2H_6$ are detected by the same sensor. In other embodiments, $CH_4$ and $C_2H_6$ are detected by different sensors or may have a different sensor response time. Thus, there may be a difference in the time that $CH_4$ and $C_2H_6$ are detected even if from the same source such as a natural gas leak. Thus, data for $CH_4$ or $C_2H_6$ may be time shifted as part of correlating the peaks in 206 and/or determining the existence of peaks at 204. Similarly, the speed of the mobile sensor platform while the sensor data was captured may also be accounted for as part of 206 and/or 204. The speed (and/or changes in speed) of the mobile sensor platform during data capture may affect the location at which the sensor data is captured, the amount of various pollutants, the quality of the data sensed and/or other features of the peaks identified. Determining whether the (optionally time shifted) $CH_4$ and $C_2H_6$ peaks are correlated may include determining whether the leading edge and trailing edges of the peak and peak widths are similar and/or are sensed at a corresponding time. Such a similar shape may indicate that $CH_4$ and $C_2H_6$ are due to a single source, such as a natural gas leak. For example, the $CH_4$ and $C_2H_6$ peaks should increase and decrease substantially together (e.g. both in distance and time) if the peaks are due to the same natural gas leak. Similarly, (optionally time shifted) $CH_4$ and $C_2H_6$ peaks sensed within a particular time period (e.g. five seconds) may be considered to be correlated in time (temporally co-located) and/or location. $CH_4$ and $C_2H_6$ peaks being temporally or geographically correlated may also indicate that the $CH_4$ and $C_2H_6$ are from the same source. Further, the relative amounts of $CH_4$ and $C_2H_6$ are indicative of the source. For example, correlated $CH_4$ and $C_2H_6$ peaks may have the appropriate ratios for refined ("dry") natural gas (e.g. leaks in delivery systems to consumers), appropriate ratios for unrefined/less refined ("wet") natural gas (e.g. leaks in upstream pipelines or wellheads), or appropriate ratios for other source (e.g. landfills or sewage systems). $CH_4$ and $C_2H_6$ peaks from the same source may have similar shapes and may be co-located in space and (optionally shifted) time. Thus, 206 may include determining the correlation between the ratios of constituents (e.g. $CH_4$ and $C_2H_6$), the peak shapes, peak locations and times. If other technique(s) are used to discriminate between sources of methane, such as isotopes, then 206 may be utilized to process data for these techniques and to correlate the findings with the methane data in lieu of or in addition to correlating $CH_4$ and $C_2H_6$ peaks. For example, the fraction of $^{13}C$ in the $CH_4$ peak may be determined. In some embodiments, the amount of $^{12}C$ in the $CH_4$ peak is also determined and a ratio of the fraction of the stable isotopes of $^{13}C$ to $^{12}C$ (i.e. $\delta^{13}C$) in the $CH_4$ peak determined. The amount of $^{13}C$ or the ratio of the stable isotopes $^{13}C$ to $^{12}C$ may be compared to known amounts of $^{13}C$ or known ratios of $^{13}C$ to $^{12}C$ in natural gas, known ratios of $^{13}C$ to $^{12}C$ in natural gas or other sources such as landfills or vehicle emissions.

In some embodiments, similar statistics are accrued for other components of the environment and correlated with $CH_4$ and $C_2H_6$ peaks. For example, pollutants or contaminants such as nitrogen dioxide ($NO_2$), carbon monoxide (CO), nitrogen oxide (NO), ozone ($O_3$), sulphur dioxide ($SO_2$), carbon dioxide ($CO_2$), volatile organic compounds (VOCs), radiation and particulate matter encountered while on the route may be measured and, where appropriate, correlated to $CH_4$, $C_2H_6$ or other gases. For example, as part of 206, it may be determined whether a CO peak is uncorrelated with the $CH_4$ and $C_2H_6$ peaks in the regions in which the $CH_4$ and $C_2H_6$ peaks are found. Natural gas does not include CO. For natural gas-related $CH_4$ sources, CO should not be correlated with $CH_4$ and $C_2H_6$ peaks. For example, the CO peak may be absent in the region and time in which $CH_4$ and $C_2H_6$ peaks are present for natural gas to be detected. In other cases, the CO peak may be present but have a different shape (e.g. different leading and trailing edges) from the $CH_4$ and $C_2H_6$ peaks for natural gas to be detected. In some embodiments, the presence of a CO peak that is correlated to the $CH_4$ and $C_2H_6$ peaks indicates that the source of the CO, $CH_4$ and $C_2H_6$ peaks is vehicle emissions. Thus, at 206 other components of the environment may also be correlated to $CH_4$ and $C_2H_6$ peaks.

Source(s) for the methane peak(s) are identified based on the correlation, at 208. $CH_4$ and $C_2H_6$ peaks from the same source may have similar shapes, may be co-located in space and (optionally shifted) time, and are present in ratios corresponding to the components of the source. Correlated $CH_4$ and $C_2H_6$ peaks may have enhancements (increases in concentration corresponding to the peak) such that the ratio of ethane to methane (i.e. $C_2H_6$ enhancement/$CH_4$ enhancement) is at least one percent ethane and not more than six percent ethane. This ratio range corresponds to refined "dry" natural gas delivered to consumers, which is approximately one through six percent ethane and approximately eighty-seven to ninety percent methane. Thus, a ratio of at least one percent and not more than six percent is consistent with the source being a refined natural gas leak. CO is not present in natural gas. Thus, in some embodiments, the source of the methane peak is determined to be a natural gas leak only if the $CH_4$ and $C_2H_6$ peaks are also uncorrelated with CO peaks. Correlated $CH_4$ and $C_2H_6$ peaks may have an ethane to methane ratio of greater than six percent. This ratio range corresponds to unrefined/less refined natural gas or other sources. This ratio of greater than six percent corresponds to other thermogenic sources such as "wet" natural gas leak in upstream pipelines, processing stations or wellheads. As discussed above, CO is not present in natural gas. Thus, the source of the methane peak may be determined to be an unrefined or less refined natural gas leak only if the $CH_4$ and $C_2H_6$ peaks are also uncorrelated with CO peaks. Correlated $CH_4$ and $C_2H_6$ peaks may have an ethane to methane ratio of less than one percent. This ratio range corresponds to sources other than natural gas, such as biogenic sources. Such a ratio of less than one percent corresponds to other sources such as biogenic sources including landfills and/or sewage systems. Similarly, the amount of $^{13}C$ or the ratio of the stable isotopes of $^{13}C$ to $^{12}C$ ($\delta^{13}C$) may be compared to known amounts of $^{13}C$ or known ratios of the stable isotopes of $^{13}C$ to $^{12}C$ in natural gas or other sources such as landfills or vehicle emissions, at 208. For example, a ratio of the stable isotopes of $^{13}C$ to $^{12}C$ of less than fifty and greater than forty per mil may be consistent with natural gas, while higher ratios are consistent with biogenic sources. At 208, therefore, the source(s) (e.g. natural gas leak, unrefined/less refined natural gas leak, other source(s) of the methane peak(s) may be identified based on the correlation.

For example, one or more of sensor systems 102 are used to passively sample the environment in a moving vehicle at 202. Sensor systems 102 thus capture $CH_4$ and $C_2H_6$ data while the vehicle is in motion and without requiring the driver to stop the vehicle to sense $C_2H_6$. The data collected by system(s) 102 may be uploaded to server 150 for processing at 204, 206 and 208. Thus, $CH_4$ and $C_2H_6$ data are processed and peaks are detected and correlated. In some embodiments, it is also determined whether there is an absence of a CO peak in the region that $CH_4$ and $C_2H_6$ peaks are correlated. If there is no CO peak and the $CH_4$ and $C_2H_6$ peaks then the source can be identified as some type of natural gas. Thus, the source of $CH_4$, as well as $C_2H_6$ and/or CO in some embodiments, can be identified. Based on the data captured, as well as other information such as wind speed; maps indicating the locations of pipelines, wellheads and processing stations; and topographical maps, the location of the source may also be determined.

Using method 200, methane peaks may be detected. The method may be extended to be used with a number of systems, such as systems 102A, 102B and 102C. Peaks from different sensor systems 102 mounted on different vehicles may be used to detect methane peaks using method 200. The data captured by one system or multiple systems may be analyzed to identify sources of methane, including but not limited to natural gas leaks in the regions in which the vehicle traveled. Method 200 may also be repeated over time internals using one or more systems. Thus, changes in the presence of natural gas leaks may be determined. For example, the effectiveness of efforts to fix the leak or the worsening of a leak may be determined. In addition, if methane is due to sources other than natural gas leaks, method 200 may indicate the identity and/or location of such sources. Thus, other actions may be taken to mitigate the emission of methane from such sources. The effectiveness of these mitigation efforts may also be monitored over time. Moreover, these benefits may be achieved while passively and more efficiently collecting environmental data.

FIG. 2B depicts an exemplary embodiment of method 250 for detecting methane using multiple sensing systems. For simplicity, only a portion of method 200 is shown. Moreover, processes in method 250 may include sub-processes and/or may be performed in another order (including in parallel). Method 250 may utilize system 100 which implements some or all of method 200. Sensor systems such as sensor system 102A, 102B, 102C and/or analogous sensor systems placed on a vehicle may be employed for detection. Thus, mobile sensing platforms may be used. Thus, data may be obtained by multiple sensor systems carried by multiple vehicles may be analyzed together for detection of methane, ethane, CO, and natural gas. Method 250 may be extended to detection of other substances and determination of leaks/sources of the substances.

Data is collected on multiple sensor systems 102 mounted on multiple vehicles and/or by multiple passes over the same region by the same vehicle having a sensor system, at 252. For example, a fleet of vehicles, each of which includes one or more sensor systems 102, may be driven over routes and data passively collected. As previously indicated, the routes may be determined to map a particular area, to focus on a region at which a leak is predicted to occur, and/or for other purposes. In some embodiments, private individuals' vehicles may include sensor systems 102. Data collection occurs while the individuals use their vehicles in daily life. In some embodiments, a combination of a fleet of vehicles and private vehicles may be used. Data is collected passively on mobile platforms at 252. Thus, users need not stop specifically to collect data, such as $C_2H_6$ data.

The data from the multiple sensor platforms 102 on multiple vehicles is analyzed to find peaks in various components as well as to identify sources for the peaks, at 254.

In some embodiments, 254 includes the sensor platforms 102 uploading data to server 150, which processes the data. Locations, times, shapes, and other data for the peaks may be determined in a manner analogous to that discussed with respect to method 200. Peaks due to natural gas or other pollutants may be identified from the combined data from multiple sensor systems on multiple vehicles. For example, the presence of $CH_4$ and $C_2H_6$ in the appropriate ratios coupled with the absence of a CO peak may be used to detect a natural gas peak. Similarly, the fraction of $^{13}C$ and/or the ratio of the stable isotopes of $^{13}C$ to $^{12}C$ in methane peaks may be used to detect a natural gas peak. In some embodiments, wind speed and direction and vehicle-based metrics (speed, direction, etc.) to detect and correlate peaks. Statistical methods may be applied to assist in detecting peaks in $CH_4$ and $C_2H_6$ as well as making a determination as to whether the peaks correspond to peak(s) in natural gas (e.g. identify the source as some type of natural gas). Thus, in addition to detecting peaks in $CH_4$ and $C_2H_6$, the peaks are correlated and sources of $CH_4$ identified based on the correlation. In some embodiments, 254 corresponds to 204, 206 and 208 being carried out for data from multiple mobile sensor platforms.

The data for sources may be analyzed to detect and characterize the sources, at 256. For example, identification of the sources (e.g. biogenic, natural gas, unrefined/less refined natural gas), geographic proximity of the peaks to the source, wind direction and speed, vehicle direction and speed, peak intensity and other peak characteristics may be analyzed to cluster peaks into a one or more potential source locations. Possible source locations may be prioritized and ranked based on their priority. The priority of a source may be determined by one or more of the intensity of natural gas signature; and frequency, persistence of detection, emission rate of the source and whether the source corresponds to a fixable emission source (e.g. a natural gas leak). Processes 252, 254 and 256 of method 250 may be repeated over time, at 258. Thus, the sources may be characterized over time. For example, the priority of the source may be adjusted based upon changes to its characteristics, detection of new sources and/or changes to other sources.

Using method 250, multiple sensor systems mounted on multiple vehicles and/or multiple passes over a region by the same vehicle may enhance detection of natural gas leaks and other sources of methane. Method 250 may also be repeated over time internals using one or more systems. Thus, changes in the presence of methane may be determined. For example, the effectiveness of efforts to fix a natural gas leak or the worsening of a natural leak may be determined. Thus, mitigation of the effects of methane and other emissions may be improved. Further, the cost of sources such as natural gas leaks may also be reduced. These benefits may be achieved while passively and more efficiently collecting environmental data.

Figure 3:
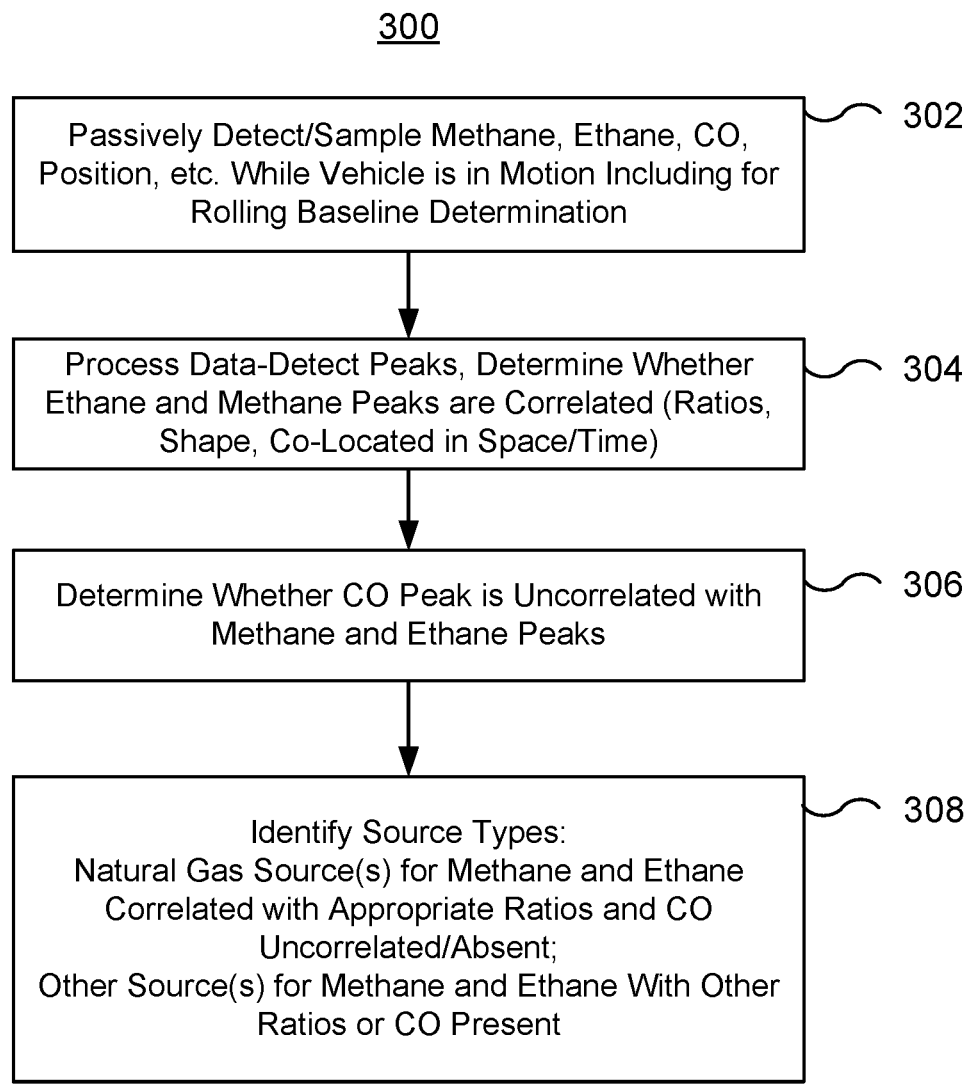
FIG. 3 is a flow chart depicting an embodiment of a method for monitoring the effect of methane on environmental quality using a mobile sensor platform.

FIG. 3 is a flow chart depicting an embodiment of method 300 for monitoring the effect of methane on environmental quality using a mobile sensor platform. For simplicity, only some portions of method 300 are described. Moreover, processes in method 300 may include sub-processes and/or may be performed in another order (including in parallel). Method 300 may utilize system 100. A sensor system such as sensor system 102A, 102B, 102C and/or analogous sensor systems placed on a vehicle may be employed for detection. Thus, a mobile platform may be used. Data from individual sensor systems are used (e.g. data from 102A is used to find peaks sensed by sensor system 102A). Further, as described below, method 300 may be carried out on multiple sensor systems, such as sensor systems 102A, 102B and 102C. Thus, data may be obtained by multiple sensor systems carried by multiple vehicles may be analyzed together for detection of methane, ethane, CO, and natural gas. Method 300 may be extended to detection of other substances and determination of leaks/sources of the substances.

Methane and ethane are passively sampled while the vehicle is in motion, at 302. In some embodiments, CO is also sampled while the vehicle is in motion. Thus, $CH_4$, $C_2H_6$ and CO may be detected by a mobile platform. In some embodiments, additional and/or other substances may also be detected at 302. Further, data is passively sampled, without user intervention at 302. For example, the driver need not stop the vehicle upon detection of methane to search for ethane. Instead, data is collected as the vehicle travels over a region and/or in motion. In some embodiments, the route taken by the vehicle at 302 is selected. For example, a route may be selected to evenly cover an area or to focus on regions at which a leak is predicted to occur. The route may be updated during operation of the vehicle. In some embodiments, there may be no route specified for the purposes of data collection. Instead, data is collected as the vehicle travels through the routes selected by the operator. For example, the sensor system may be mounted in a private individual's vehicle, in fleet vehicles and/or vehicles in a network and data collected as the vehicle travels to carry out the operator's tasks. In some embodiments, the sensor system may be mounted in vehicles in a commercial fleet, and data collected as the vehicles carry out their own tasks.

Also at 302, data for a rolling baseline determination are obtained. The baseline is utilized to determine background levels of the components of the environment of interest. For example, background levels of CO, $CH_4$, $C_2H_6$ and other constituents may be detected. In some embodiments, the baseline is determined by determining the median (or other measure of an average such as the mean) of data in a window of time ("baseline time period") around particular samples. In some embodiments, the baseline time period is at least twenty seconds and not more than four minutes. In some such embodiments, the baseline time period is at least twenty seconds and not more than forty seconds. In some embodiments, the baseline time period is at least one minute and not more than four minutes. For example, the rolling baseline for $CH_4$ may be determined using a baseline time period of thirty seconds. In some embodiments, therefore, every data point (e.g. every second for data taken each second), the median of the surrounding thirty seconds is determined" such that each data point has its own baseline centered on that point in time. This median is used as the baseline. In other embodiments, another quantity may be used for the baseline. For example, the fifth percentile instead of the median may be taken as the baseline.

The data are processed at 304. Processing the data may include detecting $CH_4$, $C_2H_6$ and CO peaks. Detecting $CH_4$, $C_2H_6$ and CO peaks includes determining the baselines for these gases and setting thresholds for detection of peaks based on the baseline. In some embodiments, a threshold for detecting peaks is set at an amount not less than the baseline. Thus, readings at or below the baseline are considered background and not utilized in determining whether a peak is present. The higher the threshold, the lower the sensitivity for peak detection. Also at 304 it may also be determined whether the $CH_4$ and $C_2H_6$ peaks are correlated. For example, the shape, timing, location and ratio of $C_2H_6$ to $CH_4$ may be determined. Thus, 304 is analogous to 204 and 206 of method 200.

It is determined whether a CO peak is uncorrelated with the $CH_4$ and $C_2H_6$ peaks in the regions in which the $CH_4$ and $C_2H_6$ peaks are found, at 306. Natural gas does not include CO. Thus, for $CH_4$ arising from natural gas emissions, CO should not be correlated with $CH_4$ and $C_2H_6$ peaks. For example, the CO peak may be absent in the region in which $CH_4$ and $C_2H_6$ peaks are present for methane arising from natural gas source(s). In other cases, the CO peak may be present but have a different shape (e.g. different leading and trailing edges) from the $CH_4$ and $C_2H_6$ peaks for methane arising from natural gas source(s) to be detected.

At 308 the source(s) of the $CH_4$ peaks are identified. For example, the sources of the $CH_4$ peaks may be identified as natural gas, unrefined/unprocessed natural gas or biogenic (e.g. from landfills). In some embodiments, the source may be identified as natural gas if correlated methane and ethane peaks are detected in the same region as a CO peak is not. For example, correlated $CH_4$ and $C_2H_6$ peaks having a ratio of ethane to methane (i.e. $C_2H_6$ enhancement/$CH_4$ enhancement) in the range of at least one percent ethane and not more than six percent ethane in combination with an uncorrelated CO peak corresponds to refined natural gas delivered to consumers. Such a ratio in combination with no correlated CO peaks results in an identification of a (refined) natural gas as a source. Thus, the methane and ethane peaks may correspond to a leak in a natural gas pipeline. Correlated $CH_4$ and $C_2H_6$ peaks having an ethane to methane ratio of greater than six percent in combination with no correlated CO peaks (i.e. uncorrelated CO peaks) results in an identification of a source that is another thermogenic source. Thus, the methane and ethane peaks may correspond to a natural gas leak in upstream pipelines, processing stations or wellheads. Correlated $CH_4$ and $C_2H_6$ peaks having an ethane to methane ratio of less than one percent regardless of CO peak correlation correspond to sources other than natural gas, such as biogenic sources including landfills and/or sewage systems. At 308, therefore, the source (dry natural gas, unrefined/less refined natural gas, or other sources) of the methane may be identified based on the correlation.

Method 300 shares the benefits of methods 200 and/or 250. Pollutants such as $CH_4$ may be detected and their sources identified. Based on the data for the $CH_4$ and $C_2H_6$ peaks and sources, emissions may be modeled, the locations of sources determined, clusters may be identified, the changes in sources (e.g. increasing or decreasing emissions) may be tracked, and the efficacy of mitigation (e.g. fixing natural gas leaks) evaluated. Thus, monitoring if environmental quality may be improved. Further, this may be achieved while passively and more efficiently collecting environmental data.

Figure 4:
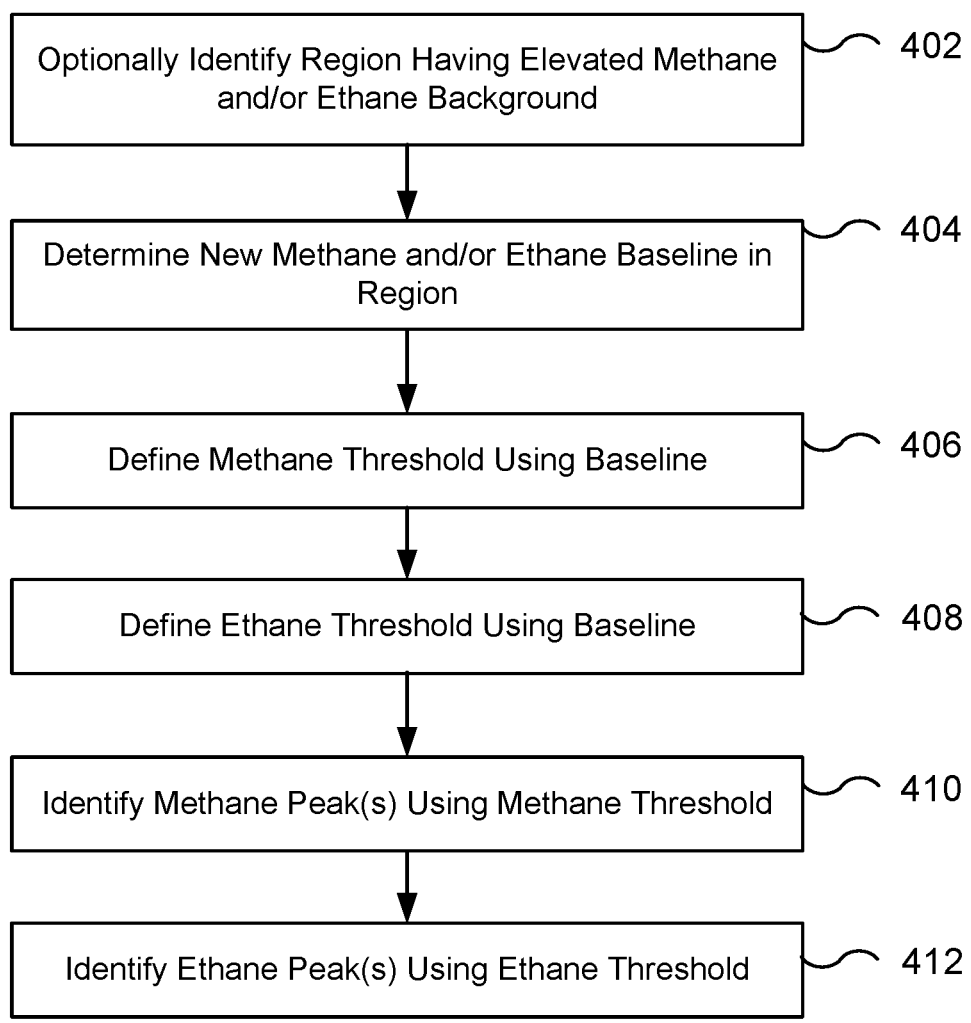
FIG. 4 is a flow chart depicting an embodiment of a method for setting a baseline for detection of gases such as methane.

FIG. 4 is a flow chart depicting an embodiment of method 400 for setting a baseline for detection of gases such as methane. For simplicity, only some portions of method 400 are described. Moreover, processes in method 400 may include sub-processes and/or may be performed in another order (including in parallel). Method 400 may utilize system 100. A sensor system such as sensor system 102A, 102B, 102C and/or analogous sensor systems placed on a vehicle may be employed for detection. Thus, a mobile platform may be used. Data from individual sensor systems are used (e.g. data from 102A is used to find peaks sensed by sensor system 102A). Further, as described below, method 400 may be carried out on multiple sensor systems, such as sensor systems 102A, 102B and 102C. Method 400 may be extended to other substances and determination of leaks/sources of the substances. Method 400 is thus described in the context of $CH_4$ and $C_2H_6$, but may be used in connection with other environmental components.

A region having an elevated $CH_4$ background and/or an elevated $C_2H_6$ background is optionally identified, at 402. Thus, 402 may be carried out if the baseline(s) are redetermined in response to large regions having elevated levels of $CH_4$ and/or $C_2H_6$. In some embodiments, 402 is utilized to be able to detect widespread peaks in $CH_4$ and/or $C_2H_6$. For example, $CH_4$ from a persistent natural gas leak in a region that has time to spread over a wide area may be inadvertently determined to be part of the background. If the $CH_4$ has spread over an area at least as large the distance the vehicle carrying the mobile sensor platform has traveled in the baseline time period described above, the baseline described above will include the $CH_4$ from the persistent leak. Thus, the $CH_4$ from the persistent leak may not be detected because it may not rise above the baseline described above. Consequently, at 402 a region corresponding to elevated levels of the component(s) of interest is defined. In some embodiments, the region is considered to have an area equal to the square of the quantity the speed of the vehicle multiplied by the existing baseline time period. The actual area traversed by the vehicle is probably less than the area of the region.

New baseline(s) $CH_4$ and/or $C_2H_6$ are determined for this region, at 404. In some embodiments, 404 includes defining a new, longer baseline time period. In some embodiments, the baseline time period may be at least twice the existing baseline time period. For example, for an existing baseline time period of thirty seconds, the new baseline time period may be one minute or more. In some embodiments, the new baseline time period is not more than eight multiplied by the existing baseline time period (i.e. four minutes). Also at 404, the median(s) for the $CH_4$ and/or $C_2H_6$ for the new baseline time period are determined. For example, each data point (e.g. every second for data taken each second), the baseline is determined using data for the surrounding minute to four minutes. Thus, each data point still has its own (rolling) baseline. These median(s) are the new baselines for $CH_4$ and/or $C_2H_6$. In some embodiments, other measures of the average for $CH_4$ and/or $C_2H_6$, such as the mean or another percentile (e.g. the fifth percentile), may be utilized as the baseline. This process may be considered to be analogous to determining the new baselines for a larger area and utilizing these baselines in at least the region defined at 402. In some embodiments, the regions are re-traversed at 404 in order to obtain new data for determining the new baseline(s). In other embodiments, existing data are used at 404.

New thresholds are set for $CH_4$ and/or $C_2H_6$ are defined at 406 and 408, respectively. The new thresholds are defined to be greater than or equal to the new baselines. Lower $CH_4$ and/or $C_2H_6$ thresholds (i.e. closer to the baseline) allow for increased sensitivity of peak detection. The new baseline(s) may be used to detect peaks, at 410 and 412. For example, the measurements for $CH_4$ in the locations for which the new baseline is used are compared to the new thresholds, at 410. Enhancements in $CH_4$ (measurements above the new $CH_4$ threshold) may be used in identifying new $CH_4$ peak(s). Similarly, enhancements in $C_2H_6$ (measurements above the new $C_2H_6$ threshold) may be used in identifying new $C_2H_6$ peaks.

Using method 400, the baselines used in detecting $CH_4$, $C_2H_6$ and/or other environmental components can be updated. Thus, baselines (i.e. rolling baselines) that not only reflect current real-world background levels of the environmental components of interest but also allow for detection of widespread, persistent peaks in $CH_4$, $C_2H_6$ and/or other environmental components can be provided. Thus, detection system performance may be improved.

Figure 5:
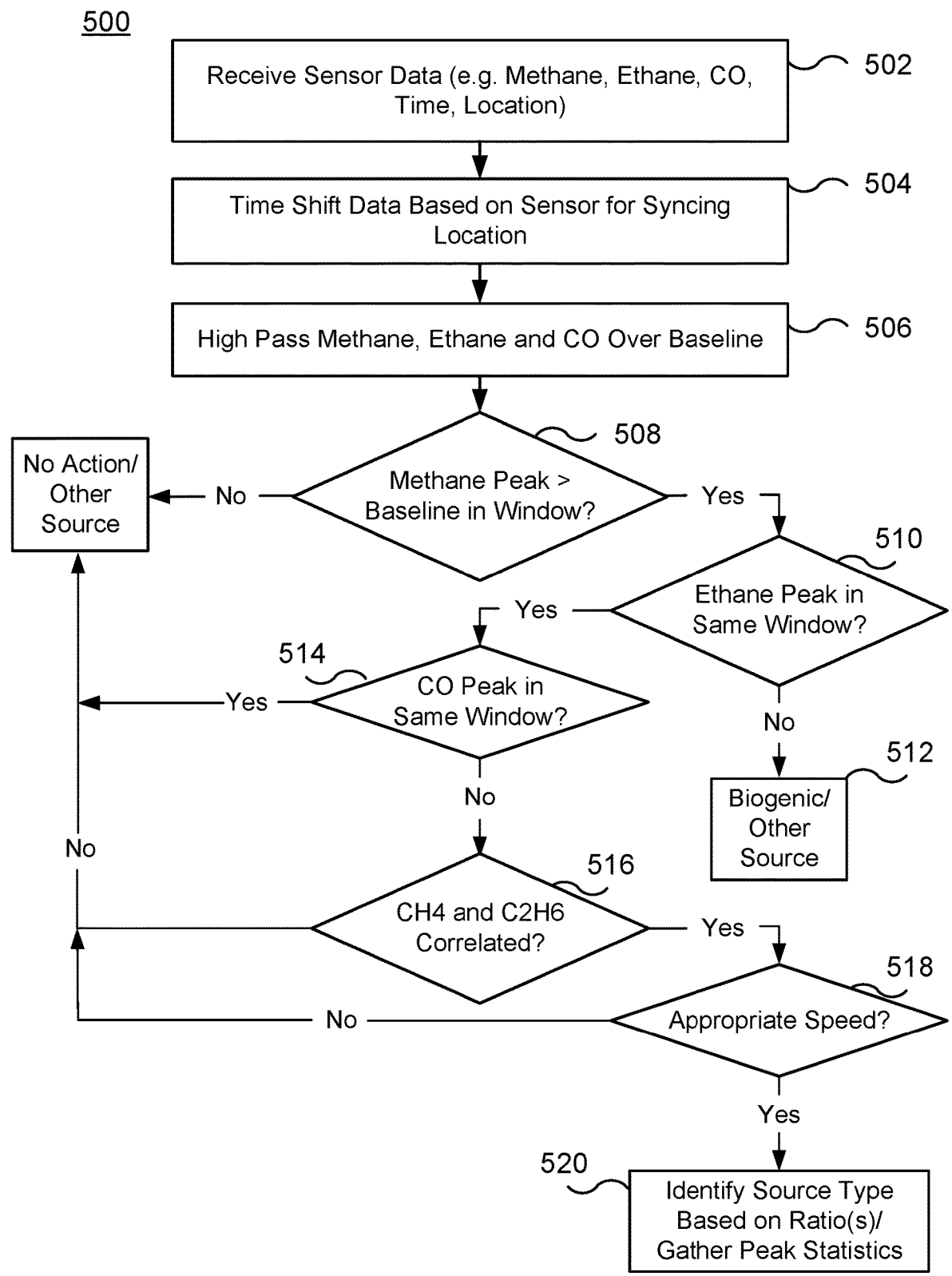
FIG. 5 is a flow chart depicting an embodiment of a method for monitoring the effect of methane on environmental quality using multiple vehicles.

FIG. 5 depicts an embodiment of method 500 for processing data provided by one or multiple mobile sensor platforms. Only some portions of method 500 are described. Moreover, processes in method 500 may include sub-processes and/or may be performed in another order (including in parallel). Method 500 may utilize data provided by system 100. A sensor system such as sensor system 102A, 102B, 102C and/or analogous sensor systems placed on a vehicle may be employed for detection. Thus, mobile platform(s) may be used. Data from individual sensor systems are used (e.g. data from 102A is used to find peaks sensed by sensor system 102A). Thus, data may be obtained by multiple sensor systems carried by multiple vehicles may be analyzed together for detection of methane, ethane, CO, and natural gas. Method 500 may be extended to detection of other substances and determination of leaks/sources of the substances.

Sensor data is received from the mobile sensor platform, at 502. Thus, $CH_4$, $C_2H_6$ and CO may be received from one or more mobile sensor platforms. In some embodiments, data from additional and/or other environmental components may also be received at 502. Further, the data received is passively sampled and includes $C_2H_6$ data captured while the sensor is in motion.

Data may be time shifted, at 504. In some embodiments, $CH_4$, $C_2H_6$ and CO are detected by different sensors and/or may have a different sensor response time. Thus, there may be a difference in the time that $CH_4$, $C_2H_6$ and CO are detected even if from the same source, such as natural gas from a leak in a pipeline. Thus, data for $CH_4$, $C_2H_6$ and/or CO may be time shifted to account for differences in sensors, sensor location, sensor response time, etc. For example, methane and ethane data may be time shifted by approximately two seconds, while CO data may be time shifted by approximately 30-40 seconds. The time shifts may be due in part to the type of sensors used to detect methane, ethane and CO and/or to time taken for the same air sample to reach sensor(s) for methane, ethane and CO.

A high pass filter is applied to the $CH_4$, $C_2H_6$ and CO data, at 506. In some embodiments, the portion of the $CH_4$, $C_2H_6$ and CO data above the respective baselines is determined at 506. Stated differently, the enhancements above background for $CH_4$, $C_2H_6$ and CO are determined. Thus, baseline fluctuations may be suppressed. In some embodiments, the filter may be a rolling median with methane and ethane data centered on a window having one extent in time and CO centered in a window having another extent in time. In some embodiments, the window for methane and ethane is approximately 30 seconds (e.g. at least fifteen seconds and not more than forty five seconds), while the window for CO may be approximately 100 seconds (e.g. at least eighty seconds and not more than one hundred and twenty seconds). In some embodiments, different windows may be used for methane, CO and/or ethane. Further, $CH_4$, $C_2H_6$ and CO peaks are also determined at 506.

At 508, it is determined whether a $CH_4$ peak exists in a particular window of data, at 508. In some embodiments, the window for methane is approximately 30 seconds. In some embodiments, a peak finding mechanism may be utilized. In some embodiments, one or more of the start/end times of a peak, the maximum absolute and enhancement peak value the average absolute and enhancement value, peak skew and kurtosis, peak length (time and distance-as vehicle/sensor system is in motion), integrated area of the enhancement peak and location of the maximum value are used to determine whether a peak exists. In some embodiments, a window length (e.g. twenty data points), a prominence (e.g. greater than 40 ppb of methane), a distance (e.g. of at least five points), a width (e.g. of at least one point) and a window length (e.g. of twenty points) may be used.

If no $CH_4$ peak is present, then no action may be taken. If, however, a $CH_4$ peak is present it is determined whether a $C_2H_6$ exists in the window, at 510. In some embodiments, the window for ethane is approximately 30 seconds and centered at the same point as for methane. In some embodiments, a peak finding mechanism may be utilized. In some embodiments, one or more of the start/end times of a peak, the maximum absolute and enhancement peak value the average absolute and enhancement value, peak skew and kurtosis, peak length (time and distance-as vehicle/sensor system is in motion), integrated area of the enhancement peak and location of the maximum value are used to determine whether a peak exists. In some embodiments, a window length (e.g. twenty data points), a prominence (e.g. greater than 2.5 ppb of ethane), a distance (e.g. of at least five points), a width (e.g. of at least one point) and a window length (e.g. of twenty points) may be used. If no ethane peak is present, then the source of the $CH_4$ peak is determined to be some source other than a natural gas source, at 512. For example, a biogenic source may be identified.

If a $CH_4$ peak is found, then it is determined whether a CO peak is present in the window, at 514. In some embodiments, the window for CO may be approximately 100 seconds but centered on the same time as the methane peak. In some embodiments, a peak finding mechanism may be utilized. In some embodiments, one or more of the start/end times of a peak, the maximum absolute and enhancement peak value the average absolute and enhancement value, peak skew and kurtosis, peak length (time and distance-as vehicle/sensor system is in motion), integrated area of the enhancement peak and location of the maximum value are used to determine whether a peak exists. In some embodiments, a window length (e.g. one hundred and twenty data points), a prominence (e.g. greater than 0.1 ppm of CO), a distance (e.g. of at least five points), a width (e.g. of at least one point) and a window length (e.g. of twenty points) may be used. Thus, it is determined whether the $CH_4$ peak and $C_2H_6$ peak are uncorrelated with a CO peak. If a CO peak is found in the window, then the source is not a natural gas source. Thus, another source is identified or no action is taken.

If no CO peak is found or the CO peak is not correlated with the $CH_4$ peak and the $C_2H_6$, then it is determined whether $CH_4$ peak and the $C_2H_6$ are correlated, at 516. As discussed above, the peak shape, location, and ratio of ethane to methane may be checked. High correlation in shape between methane and ethane suggests that both signals originate from the same gas plume. In some embodiments. 0.75-0.8 may be used as a cutoff for absolute and/or enhancement correlations. In other embodiments, other cutoffs may be used.

If the peaks are not correlated, no action is taken or another source of methane is identified. If the peaks are correlated, then the vehicle speed and direction may be checked, at c. The speed and direction of the vehicle are checked to determine that they are appropriate for detection of $CH_4$, $C_2H_6$ and CO. In some embodiments, the mobile sensor platform speed is at least five miles per hour. In some embodiments, the speed is at least ten miles per hour. For example, the speed of the vehicle may be at least three meters per second and not more than fifteen meters per second in some embodiments (6 mph-34 mph). In some embodiments, lower speeds (e.g. including zero) are excluded to ensure that data from the vehicle being parked or otherwise not in motion for longer periods of time are excluded. Thus, peaks corresponding to speeds outside of this window may be removed at 518. In some embodiments, peaks where the time length of a peak exceeds 25 seconds are excluded at 518. Thus, the peak detection window is 20 seconds in some embodiments. Windows that are much longer than this may result in data gaps within the "peak". Consequently, peaks where the distance covered during a peak exceeds 200 meters may be excluded in some embodiments. In some embodiments, such widespread peaks may result in the adjustment of the baseline described with respect to FIG. 4. The limitations on window and distance may be highly correlated to vehicle speed. So the speed filter of 518 may remove a large number of these issues. But the optional window/distance filter for data may optionally be used to provide an additional technique for excluding a highly dispersed plume.

If the speed of the vehicle is appropriate, then the source of the methane peak is identified based on the ratios, at 520. In addition, statistics on the peak (size, location, time, etc.) are collected.

Method 500 shares the benefits of methods 200 and 300. Using method 500, methane peaks may be detected and sources of methane peaks determined. Changes in methane sources may also be monitored. For example, the effectiveness of efforts to fix the leak or the worsening of a leak may be determined. In addition, if the methane peak is due to sources other than natural gas leaks, method 500 may indicate the identity and/or location of such sources. Thus, other actions may be taken to mitigate the emission of methane from such sources. The effectiveness of these mitigation efforts may also be monitored over time. Moreover, these benefits may be achieved while passively and more efficiently collecting environmental data.

Figure 6:
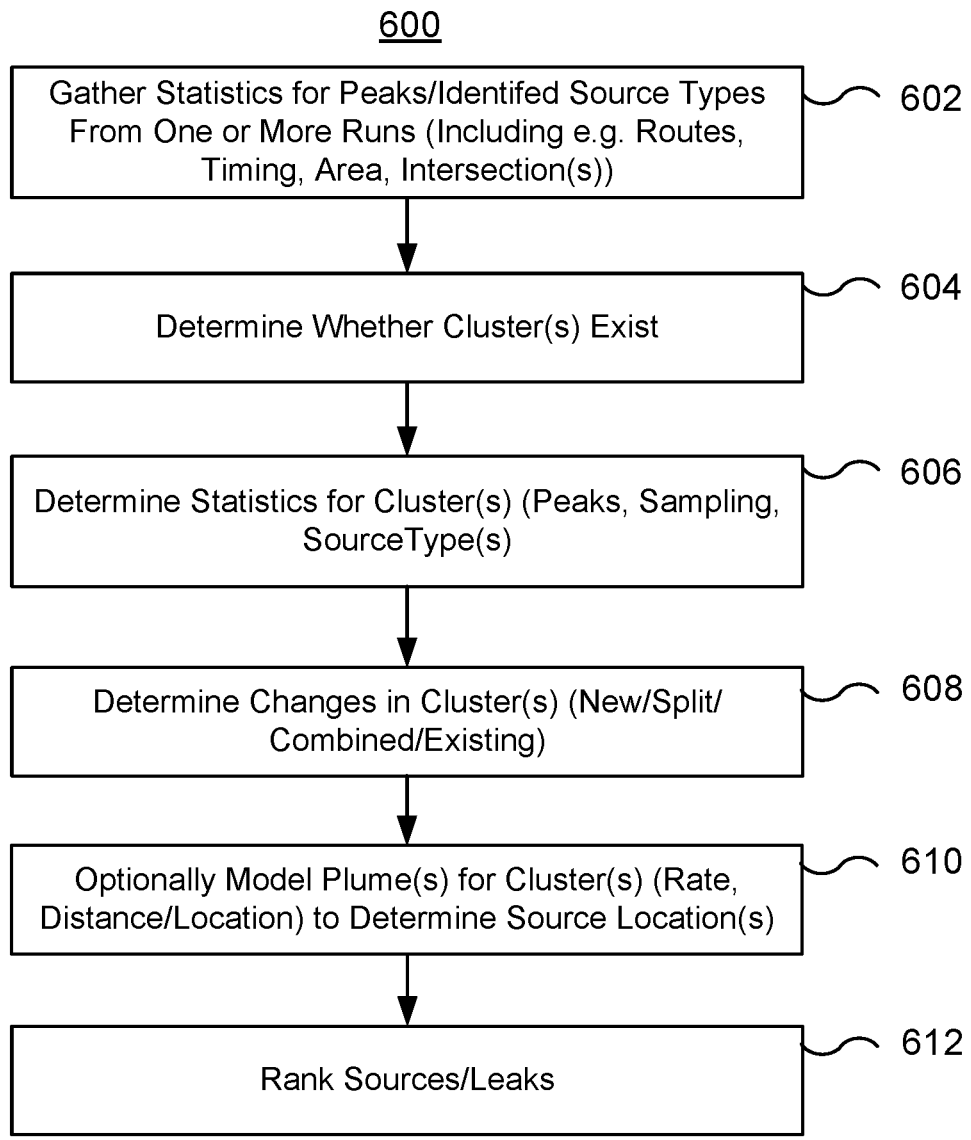
FIG. 6 is a flow chart depicting an embodiment of a method for processing environmental quality data using multiple vehicles.

FIG. 6 is a flow chart depicting an embodiment of a method for processing air quality data using multiple vehicles. Only some portions of method 600 are described. Moreover, processes in method 600 may include sub-processes and/or may be performed in another order (including in parallel). Method 600 may utilize data provided by system 100. A sensor system such as sensor system 102A, 102B, 102C and/or analogous sensor systems placed on a vehicle may be employed for detection. Thus, mobile platform(s) may be used. Data from individual sensor systems are used (e.g. data from 102A is used to find peaks sensed by sensor system 102A). Thus, data may be obtained by multiple sensor systems carried by multiple vehicles may be analyzed together for detection of methane, ethane, CO, and natural gas. Method 600 may be extended to detection of other substances and determination of leaks/sources of the substances.

Figure 7:
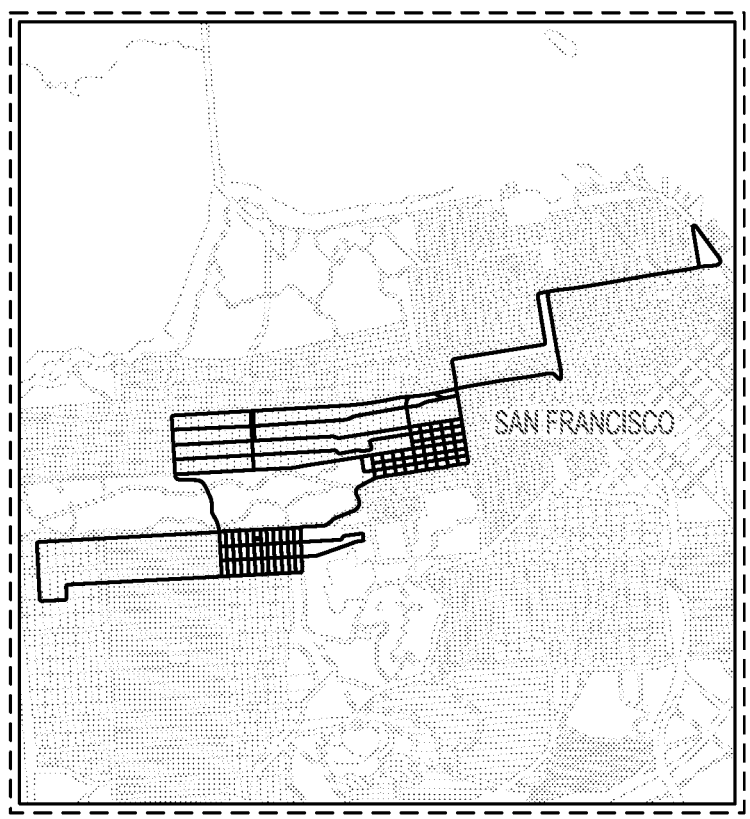
FIG. 7 depicts embodiments of various possible routes.

Additional statistics may be gathered for peaks, at 602. Such information may relate to detection rates and co-occurrence of peaks. For example, in order to account for the context in which detection was made, the vehicle on which the sensor system was mounted, the vehicle speed during the $CH_4$ (and, optionally $C_2H_6$) peak window, the wind speed during the $CH_4$ (and, optionally $C_2H_6$) peak window and the wind direction during the $CH_4$ (and, optionally $C_2H_6$) peak window may be measured or otherwise determined. In addition, the number of times a location was driven relative to the number of times a peak was detected may also be used to provide context on sampling of the location. For example, it may be desirable to determine how many times the area was driven in order to notice the event/peak detection. A high ratio of passes to detections could indicate things such as a weak or intermittent source, or erroneous measurements. Determining this rate relies on the quantification of how many times a particular location was passed over the course of sampling on a given day. At 602, the routes of each vehicle that was measuring $CH_4$ on the day of interest are desired to be known. This may be determined by line segment(s) of the sequential GPS positions throughout the day. In some embodiments, Sequential points separated by more than 30 seconds are not connected. A line simplification algorithm may be used to reduce the number of coordinates. The routes may be collected into a multi-line string. For example, FIG. 7 depicts embodiments of various routes.

Figure 8:
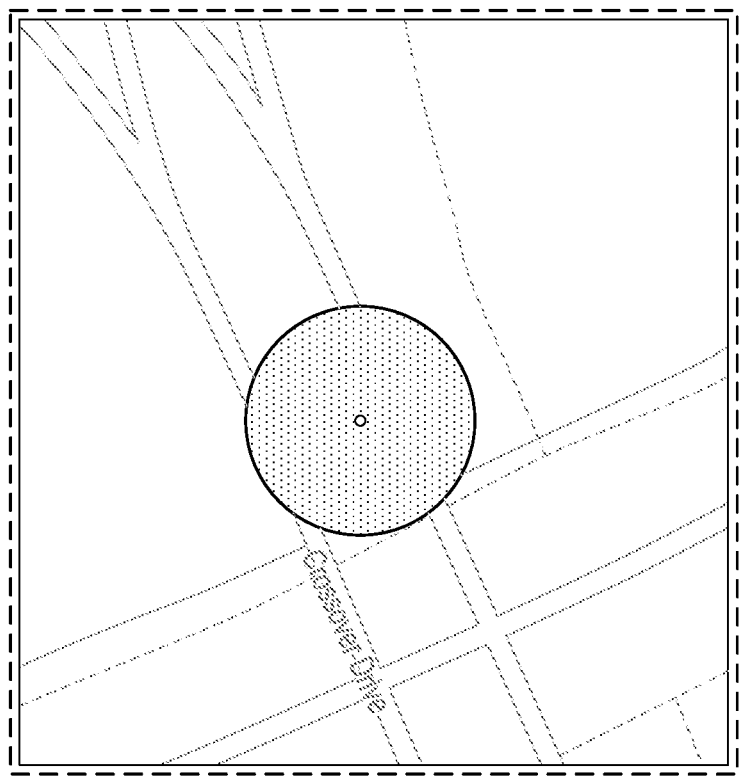
FIG. 8 depicts an embodiment of a possible area.

The area over which a pass would be considered a repetition relative to the peak being evaluated may also be defined at 602. In some embodiments, a circular buffer surrounding the methane peak location is defined. For example, in some embodiments, fifteen meters is the radius. But other sizes and/or shapes might be used. FIG. 8 depicts an embodiment of the area.

Intersection evaluation may also be performed at 602 to determine the number of times a mobile sensor platform passed a particular location of interest. With the route lines and areas of interest, a simple intersection of the two provides the segments of all routes on the day of interest that passed through the location of interest. Counting these segments yields the number of times a mobile sensor platform passed the location. In some embodiments, another mechanism for assigning the number of passes may be used. For example, the number of passes is based on a nearby segment having the most passes. In a similar manner, other peak points that fall within the location buffer may also be recorded.

Clustering of detected natural gas sources, methane peaks, ethane peaks and/or other peaks may also be performed at 606, 606, and 608. Clustering may provide a better indication of the size and location of methane sources (e.g. natural gas leaks) as well as how such sources change. Thus, it is determined whether clusters exist, at 604. Data gathered at 602 and and/or in the methods 200, 250, 300, 400, 500 and/or 600 may be used at 604.

Figure 9:
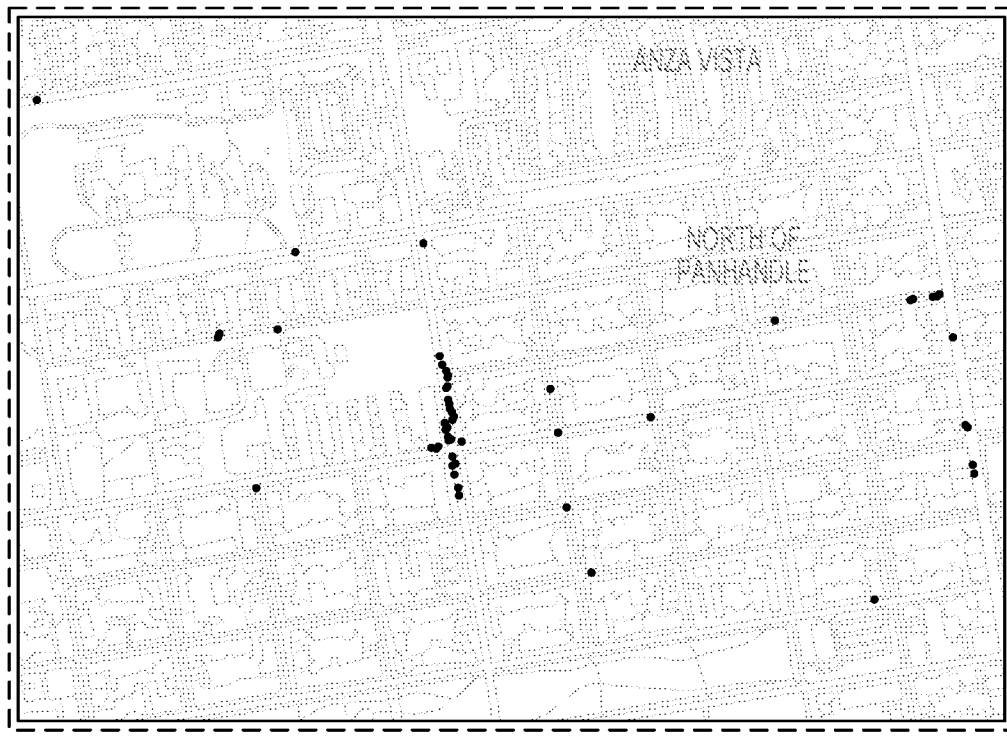
FIGS. 9-10 depict embodiments of locations of peaks and the corresponding cluster.
Figure 10:
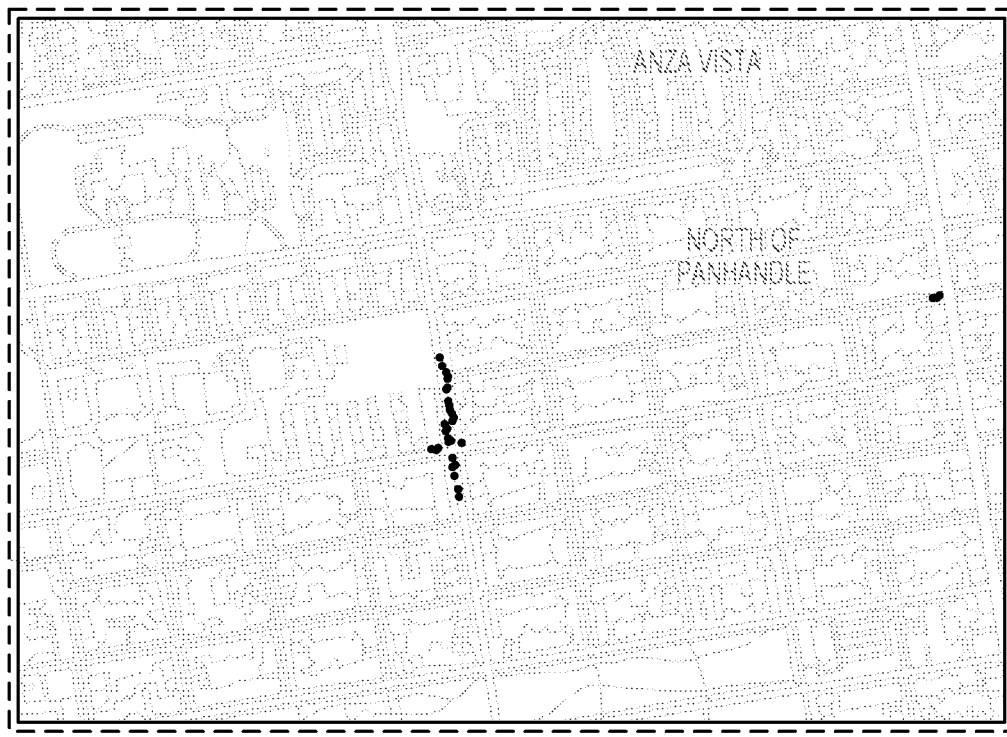

In some embodiments, a clustering mechanism such as DBSCAN may be used. Thus, the clustering may be based on the minimum number of points in a peak, the maximum distance between two peaks for the peaks to be considered part of the same cluster, and the distance metric which is a measure of how the distances between samples are calculated. In some embodiments, the minimum number of points selected may be as small as three. In other embodiments, other minimum numbers of points might be used. The distance is the maximum distance between two samples for them to be considered part of the same cluster. In some embodiments, the distance is twenty-five meters. However, in other embodiments, other distances may be used. In some embodiments, the Haversine distance is used as the distance metric. Other measures may be used in other embodiments. For example, FIGS. 9 and 10 are exemplary embodiments of individual peaks detected on a map (each circle is a peak in FIG. 9) and clusters determined from the peaks (each circle in FIG. 10 is a cluster from the peaks shown in FIG. 9). In some embodiments, the weighted centroid of the cluster of peaks is defined as the cluster location. The weight for each location is the enhancement (e.g. magnitude) of the peak at that location. Thus, the location of the cluster is more influenced by the largest peak in the cluster.

Figure 11:
FIGS. 11-12 depict embodiments of locations of clusters and the corresponding cluster area.
Figure 12:
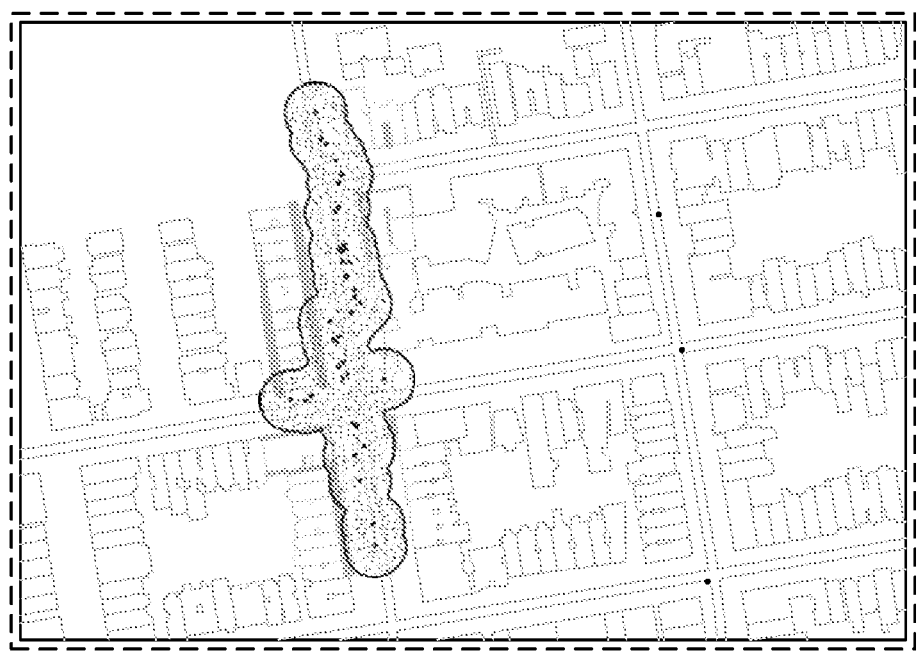

Once points are grouped into clusters, an area encompassed by the cluster may also be defined as part of 604. This may be accomplished by buffering the individual points and combining these buffers into a single polygon. In some embodiments, this is parameterized with a buffer distance of 15 meters. Other distances may be used. In addition, other methods could be used to define the cluster area. For example, a bounding box or convex hull may be utilized, but may generally overestimate the cluster area. FIGS. 11 and 12 depict an exemplary embodiment of clusters (FIG. 11) and the corresponding cluster area (FIG. 12).

In some embodiments, once clusters are defined, various metrics may be derived for each cluster as part of 606. In some embodiments, the metrics calculated for each cluster include: sampling details, peak summaries and source summaries. Sampling details provide descriptions of the cluster itself and information related to sampling effort. Peak summaries provide summary metrics of a few selected peak fields. Source summaries provide a summary of metrics related to the calculated/determined leak rate and distance estimated from the data. Additional and/or other metrics may be determined in other embodiments. In some embodiments, for example, the sampling details may include the peak count, the number of passes, the detection rate, the number of days having a peak, the number of days driven, the average enhancement for each peak, the enhancement standard of deviation, the average maximum values, the maximum standard of deviation, the time or number of passes since anything within the cluster has been detected, and the number of peaks within a cluster detected within a defined number of passes. For the peak count, the peak count includes the number of peaks (e.g. for methane) included in the cluster. The concurrent peak count includes the number of peaks where the methane peak and the ethane peak are concurrent (e.g. occurring at substantially the same time and location and, in some embodiments, which are correlated as described above). The number of passes is the number of times the vehicle(s) having mobile sensor platform(s) was/ were driven through the cluster. The detection rate (all) is the ratio of the peak count for methane to the total number of passes. The detection rate (concurrent) is the ratio of the concurrent peak count to the total number of passes. The number of days with a peak is the unique dates when a peak was detected for the cluster. The number of days driven is the unique dates when the cluster was driven through at least one. The average enhancement for each peak may be calculated for methane and ethane. The average enhancement for each gas may be determined. Similarly, the enhancement standard of deviation is the standard of deviation for each gas and each peak. The average maximum value is the average of the maximum values across the peaks for each gas. Similarly, the maximum standard of deviation is the standard of deviation in the maximum values of the peak of reach gas. Other and/or additional statistics may be determined in other embodiments.

Also as part of 606, statistics may also be calculated for each peak and/or identified source (e.g. each combination of ethane and methane peaks which results in identification of a source). Thus, source summaries may also be provided. These include the average leak rate, the standard of deviation for the leak rate, the average distance and the standard of deviation for distance. The average leak rate is the leak rate derived from each peak or combination of concurrent ethane and methane peaks. The standard of deviation in the leak rate may be based on the uncertainty in estimates made from individual peaks or combination of concurrent ethane and methane peaks. The average distance is the average distance between the calculated position of the leak and the detection location of the peak/combination of concurrent peaks. The standard deviation in the distance is based on the uncertainty of estimates made from individual peaks. Thus, in addition to determining the locations of sources/leaks based upon peak detection, statistics related to the determination may be provided.

Changes in clusters over time may also be tracked, at 608. Thus, clusters may be identified as new, existing, a combination or a split. New cluster is a cluster that is created from peaks that have not previously been components of other clusters. An existing cluster consists of peaks associated with the same cluster identification. Thus, the existing cluster does not include new peaks or missing peaks. A cluster combination includes peaks that were previously in multiple different clusters. A cluster split occurs when multiple clusters are formed from peaks associated with the same previous cluster. Thus, the changes in clusters over time may be tracked.

Figure 13:
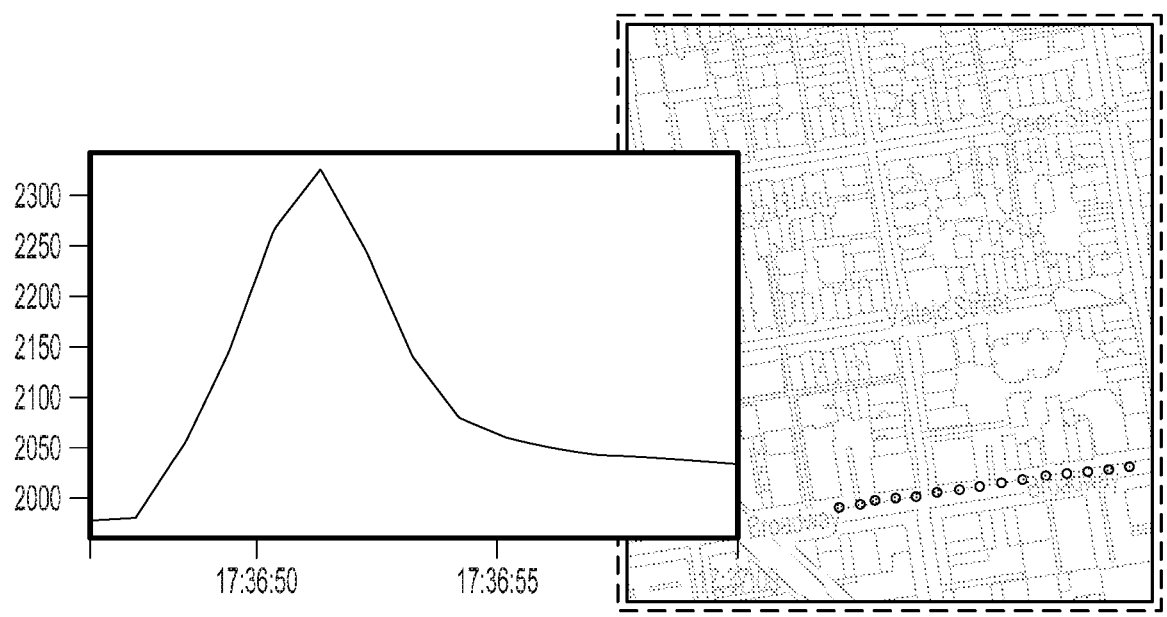
FIGS. 13-16 depict embodiments of peaks used for plume modeling.
Figure 14:
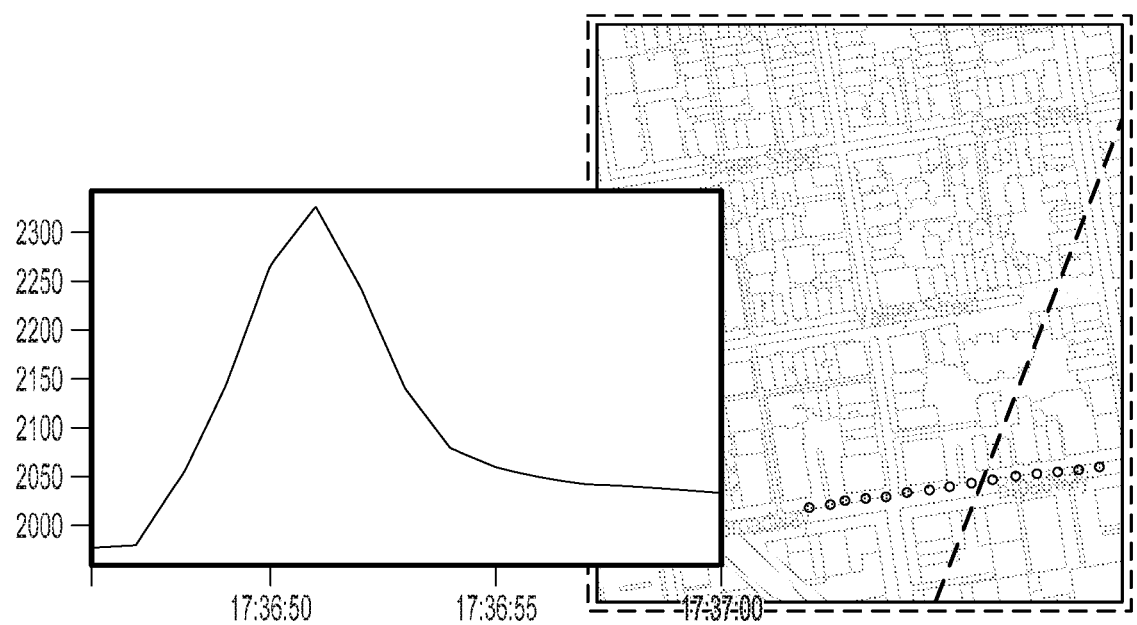
Figure 15:
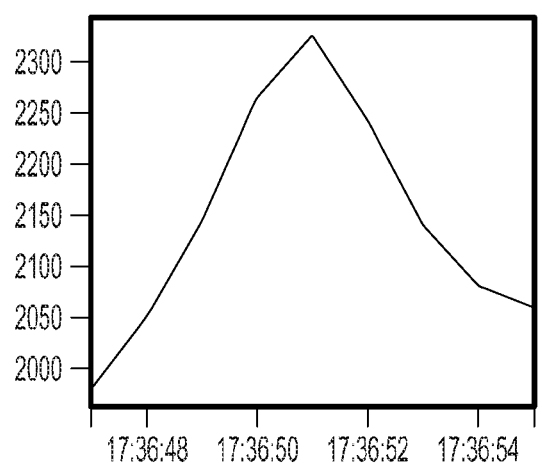
Figure 15:
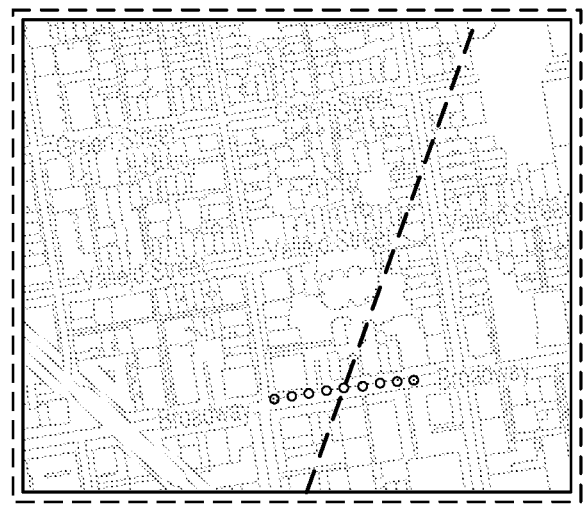
Figure 16:
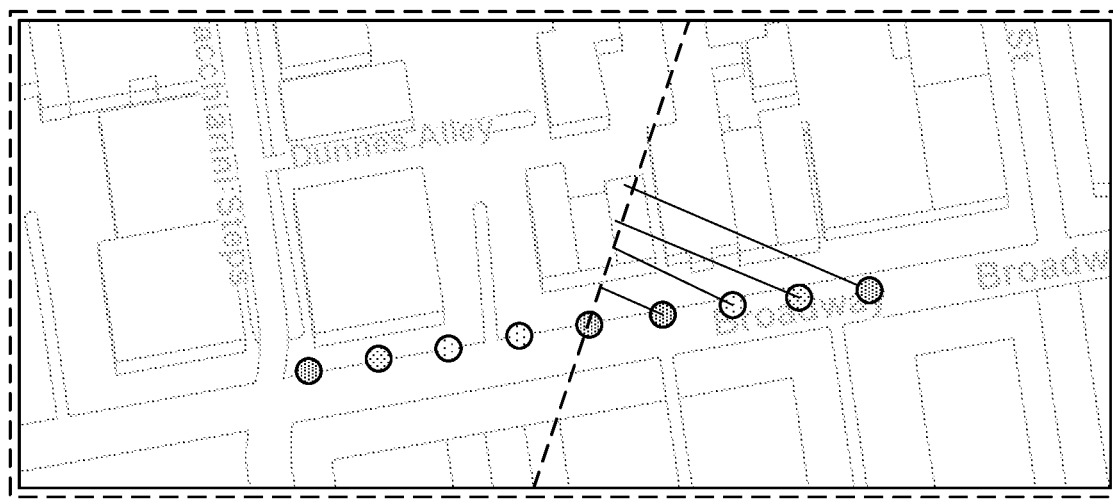

In addition, plumes may be modeled for clusters, at 610. Plume modeling allows for the locations and sizes of the sources corresponding to the peaks in the cluster to be determined. The plume is modeled to determine the emission rate of a methane leak leading to the series of peaks observed and the corresponding sources identified as described herein. Assuming that a leak leads to a plume with specific characteristics, and that measurements are a representative cross section of this plume, the conditions (leak rate and distance) that theoretically produced the conditions we measured can be solved for. In some embodiments, a Gaussian plume model is used. For example, the following procedure may be used to determine the location of a natural gas leak corresponding to peaks described herein. Using the methods described herein, such as method 200, peaks may be classified as having a natural gas source. One peak and a series of peak locations are shown in FIG. 13. A theoretical plume centerline is derived from the maximum in methane (ethane, and/or natural gas) observed and the average wind direction. This is shown in FIG. 14. The peak is subsampled to ±a particular number of seconds from the maximum (e.g. four seconds) as shown in FIG. 15. The distance of each data point from the plume centerline (the off-axis distance) is determined, as shown in FIG. 16. The dispersion coefficients of the Gaussian model are determined for the plume. This may include determining the Pasquill atmospheric stability class from the time of day and wind speed. Solar radiation, cloud cover and other environmental conditions may also be taken into account. The horizontal and vertical dispersion coefficients are derived at various distances from the source for each atmospheric stability class. The source of the plume is still considered unknown. The two remaining unknowns are solved for. The remaining unknowns are leak rate and leak distance (which provides the unknown dispersion coefficients). These unknowns may be solved for using the best fit to the $CH_4$ peak(s) detected. Fitting constraints include that both the leak rate and leak distance are greater than zero. The inputs may include the concentration of the pollutant (e.g. methane) in, for example, $g/m^3$ (converted from ppb), wind speed (e.g. in m/s), distance from the centerline (e.g. in meters), and the dispersion coefficient (e.g. in meters). The output of the best fit may include the distance in meters and the emission rate, for example in g/s (which can be converted to cfph). In some embodiments, controlled testing data as well as field trials may be used to create a linear relationship between observed peak sizes and leak size. In some embodiments, this process may be carried out for $CH_4$ only. In such embodiments, the process is carried out after the correlation (including determining the appropriate ratio range for $CH_4$ and $C_2H_6$) has been carried out.

The leaks (e.g. locations of sources) determined at 610 may be ranked, at 612. In some embodiments, ranking the sources may take into account contextual data such as population density and the proximity of high-density and/or high-priority sites (e.g. schools, churches, etc.) as well as other risk factors. Thus, using the location and emission rate, the severity of the leak and the relative need for mitigation may be determined.

Using method 600, methane peaks may be clustered, and leaks or other emitters of methane may be located and prioritized. Changes in methane sources may also be monitored. For example, the effectiveness of efforts to fix the leak or the worsening of a leak may be determined. In addition, if methane is due to sources other than natural gas leaks, method 600 may still allow for location, monitoring, and ranking of such sources. Thus, other actions may be taken to mitigate the emission of methane from such sources. The effectiveness of these mitigation efforts may also be monitored over time. Moreover, these benefits may be achieved while passively and more efficiently collecting environmental data.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method for monitoring air quality, comprising:
    measuring ethane and methane using a mobile sensor platform to provide sensor data, the sensor data including methane data and ethane data captured at a nonzero mobile sensor platform speed;
    identifying at least one methane peak and at least one ethane peak in the sensor data;
    determining a plurality of correlations, the plurality of correlations being between the at least one ethane peak and the at least one methane peak and between at least one amount of $^{13}C$ and the at least one methane peak; and
    identifying a source for the at least one methane peak based on the plurality of correlations, comprising:
        determining whether a first correlation exists between the at least one ethane peak and the at least one methane peak and a second correlation exists between the at least one amount of $^{13}C$ and the at least one methane peak; and
        in response to a determination that the first correlation exists between the at least one ethane peak and the at least one methane peak and the second correlation exists between the at least one amount of $^{13}C$ and the at least one methane peak, determining the source based on a first amount of the at least one amount of $^{13}C$ or a second amount of the at least one amount of $^{13}C$, the first amount being different from the second amount.

2. The method of claim 1, wherein the measuring ethane and methane further includes:
    measuring the ethane and the methane using the mobile sensor platform while the mobile sensor platform is in motion such that the methane data and ethane data are captured at a mobile sensor platform speed of at least five miles per hour.

3. The method of claim 2, further comprising:
    accounting for the mobile sensor platform speed.

4. The method of claim 2, wherein the determining further includes:
    identifying a ratio range of ethane to methane; and
    wherein the identifying the source further includes identifying the source based on the ratio range.

5. The method of claim 4, wherein the identifying the source for the at least one ethane peak and the at least one methane peak further includes:
    determining a natural gas source is present if the ratio range is at least one percent and not more than six percent;
    determining a thermogenic source is present if the ratio range is greater than six percent; and
    determining a non-natural gas source is present if the ratio range is less than one percent.

6. The method of claim 5, further comprising:
    determining whether a coincident CO peak is lacking for the at least one methane peak and the at least one ethane peak; and
    wherein the identifying the source further includes determining a natural gas source is present only if the coincident CO peak is also lacking.

7. The method of claim 2, wherein the sensor data includes only ethane data and methane data for the mobile sensor platform having the nonzero mobile sensor platform speed.

8. The method of claim 2, further comprising:
    performing clustering for at least one of the at least one methane peak and the at least one ethane peak.

9. The method of claim 7, further comprising:
    determining a source location based on the source, the at least one methane peak, the at least one ethane peak, a wind speed and a wind direction.

10. The method of claim 2, wherein the identifying further includes:
    identifying a region corresponding to elevated methane and elevated ethane and having an area corresponding to a square of a quantity, the quantity being the mobile sensor platform speed multiplied by a baseline time period, the baseline time period being at least thirty seconds;
    evaluating a methane baseline and an ethane baseline for the sensor data in at least the region, the methane baseline corresponding to a first median of methane data for the at least the region using new time period greater than the baseline time period, the ethane baseline corresponding to a second median of ethane data for the at least the region using new time period greater than the baseline time period, the ethane baseline;
    defining a methane threshold equal to at least the methane baseline;
    defining an ethane threshold equal to at least the ethane baseline;
    identifying a methane peak as sensor data including multiple methane readings in the region greater than the methane threshold, the methane peak having a location based on a methane weighted average of the multiple methane readings; and
    identifying an ethane peak as sensor data including multiple ethane readings in the region greater than the ethane threshold, the ethane peak having a location based on an ethane weighted average of the multiple ethane measurements.

11. A system, comprising:
    a processor configured to:
        receive sensor data captured using a mobile sensor platform, the sensor data including ethane data and methane data captured at a mobile sensor platform speed of at least five miles per hour;

identify at least one methane peak and at least one ethane peak in the sensor data;

determine a plurality of correlations, the plurality of correlations being between the at least one ethane peak and the at least one methane peak are correlated and between at least one amount of $^{13}C$ and the at least one methane peak; and identify a source for the at least one methane peak based on the plurality of correlations, comprising to:

determine whether a first correlation exists between the at least one ethane peak and the at least one methane peak and a second correlation exists between the at least one amount of $^{13}C$ and the at least one methane peak; and in response to a determination that the first correlation exists between the at least one ethane peak and the at least one methane peak and the second correlation exists between the at least one amount of $^{13}C$ and the at least one methane peak, determine the source based on a first amount of the at least one amount of $^{13}C$ or a second amount of the at least one amount of $^{13}C$, the first amount being different from the second amount; and a memory coupled to the processor and configured to provide the processor with instructions.

12. The system of claim 11, wherein the processor is further configured to:
account for the mobile sensor platform speed.

13. The system of claim 12, wherein to determine the plurality of correlations, the processor is further configured to:
identify a ratio range of ethane to methane; and
wherein to identify the source, the processor is further configured to identify the source based on the ratio range.

14. The system of claim 13, wherein to identify the source for the at least one ethane peak and the at least one methane peak, the processor is further configured to:
determine a natural gas source is present if the ratio range is at least one percent and not more than six percent;
determine a thermogenic source is present if the ratio range is greater than six percent; and
determine a non-natural gas source is present if the ratio range is less than one percent.

15. The system of claim 12, wherein the processor is further configured to:
determine whether a coincident CO peak is lacking for the at least one methane peak and the at least one ethane peak; and
wherein to identify the source, the processor is further configured to determine the natural gas source is present only if the coincident CO peak is also lacking.

16. The system of claim 12, wherein the processor is further configured to:
perform clustering for at least one of the at least one methane peak and the at least one ethane peak.

17. The system of claim 12, wherein the processor is further configured to:
determine a source location based on the source, the at least one methane peak, the at least one ethane peak, a wind speed and a wind direction.

18. The system of claim 12, wherein to identify, the processor is further configured to:
identify a region corresponding to elevated methane and elevated ethane and having an area corresponding to a square of a quantity, the quantity being the mobile sensor platform speed multiplied by a baseline time period, the baseline time period being at least thirty seconds;

evaluate a methane baseline and an ethane baseline for the sensor data in at least the region using a new time period greater than the baseline time period, the methane baseline corresponding to a first median of methane data for the at least the region, the ethane baseline corresponding to a second median of ethane data for the at least the region;

define a methane threshold equal to at least the methane baseline;

define an ethane threshold equal to at least the ethane baseline;

identify a methane peak as sensor data including multiple methane readings in the region greater than the methane threshold, the methane peak having a location based on a methane weighted average of the multiple methane readings; and identify an ethane peak as sensor data including multiple ethane readings in the region greater than the ethane threshold, the ethane peak having a location based on an ethane weighted average of the multiple ethane measurements.

19. A computer program product for monitoring air quality, the computer program product being embodied in a tangible computer readable storage medium and comprising computer instructions for:

receiving sensor data captured using a mobile sensor platform, the sensor data including ethane data and methane data captured at a mobile sensor platform speed of at least five miles per hour;

identifying at least one methane peak and at least one ethane peak in the sensor data;

determining a plurality of correlations, the plurality of correlations being between the at least one ethane peak and the at least one methane peak and between at least one amount of $^{13}C$ and the at least one methane peak; and identifying a source for the at least one methane peak based on the plurality of correlations, comprising:

determining whether a first correlation exists between the at least one ethane peak and the at least one methane peak and a second correlation exists between the at least one amount of $^{13}C$ and the at least one methane peak; and in response to a determination that the first correlation exists between the at least one ethane peak and the at least one methane peak and the second correlation exists between the at least one amount of $^{13}C$ and the at least one methane peak, determining the source based on a first amount of the at least one amount of $^{13}C$ or a second amount of the at least one amount of $^{13}C$, the first amount being different from the second amount.

20. The computer program product of claim 19, wherein the computer instructions for determining the plurality of correlations further include computer instructions for:
identifying a ratio range of ethane to methane; and
wherein the computer instructions for identifying the source for the at least one ethane peak and the at least one methane peak identify the source based on the ratio range, computer instructions for identifying the source further including computer instructions for:
determining a natural gas source is present if the ratio range is at least one percent and not more than six percent;

determining a thermogenic source is present if the ratio range is greater than six percent; and determining a non-natural gas source is present if the ratio range is less than one percent.

* * * * *